(12) United States Patent
Cholli et al.

(10) Patent No.: US 8,039,673 B2
(45) Date of Patent: Oct. 18, 2011

(54) MACROMOLECULAR ANTIOXIDANTS COMPRISING DIFFERING ANTIOXIDANT MOIETIES: STRUCTURES, METHODS OF MAKING AND USING THE SAME

(75) Inventors: Ashok L. Cholli, Chelmsford, MA (US); Rajesh Kumar, Groton, CT (US)

(73) Assignee: Polnox Corporation, Lowell, MA (US)

( * ) Notice: Subject to any disclaimer, the term of this patent is extended or adjusted under 35 U.S.C. 154(b) by 135 days.

(21) Appl. No.: 12/319,282

(22) Filed: Jan. 5, 2009

(65) Prior Publication Data

US 2009/0184294 A1 Jul. 23, 2009

Related U.S. Application Data

(63) Continuation of application No. PCT/US2007/015177, filed on Jun. 29, 2007.

(60) Provisional application No. 60/818,876, filed on Jul. 6, 2006.

(51) Int. Cl.
*C07C 213/00* (2006.01)
*C07C 215/00* (2006.01)
*C07C 217/00* (2006.01)
*C07C 211/00* (2006.01)
*C09K 15/00* (2006.01)
*C09K 15/16* (2006.01)
*C09K 15/22* (2006.01)

(52) U.S. Cl. ........ 564/350; 564/336; 564/348; 252/397; 252/401; 252/403; 252/405

(58) Field of Classification Search .................. 252/403, 252/397, 401, 405; 564/336, 348, 350
See application file for complete search history.

(56) References Cited

U.S. PATENT DOCUMENTS

| | | | |
|---|---|---|---|
| 3,116,305 A | 12/1963 | Morris et al. | |
| 3,294,836 A | 12/1966 | Peterson et al. | |
| 3,441,545 A | 4/1969 | Blatz et al. | |
| 3,459,704 A | 8/1969 | Peterson et al. | |
| 3,557,245 A | 1/1971 | Phillips et al. | |
| 3,632,785 A | 1/1972 | Bornstein | |
| 3,645,970 A | 2/1972 | Kleiner | |
| 3,649,667 A | 3/1972 | Song et al. | |
| 3,655,831 A | 4/1972 | Friedman | |
| 3,870,680 A | 3/1975 | Schurdak | |
| 3,907,939 A | 9/1975 | Robin et al. | |
| 3,953,402 A | 4/1976 | Kline | |
| 3,965,039 A | 6/1976 | Chaplits et al. | |
| 3,983,091 A | 9/1976 | Gloth et al. | |
| 3,994,828 A | 11/1976 | Zaffaroni | |
| 3,996,160 A | 12/1976 | Dale et al. | |
| 3,996,198 A | 12/1976 | Wang et al. | |
| 4,054,676 A | 10/1977 | Weinshenker et al. | |
| 4,094,857 A | 6/1978 | Wolfe, Jr. | |
| 4,096,319 A | 6/1978 | Willette et al. | |
| 4,097,464 A | 6/1978 | Kline | |
| 4,098,829 A | 7/1978 | Weinshenker et al. | |
| 4,107,144 A | 8/1978 | Russell et al. | |
| 4,136,055 A | 1/1979 | Lyons | |
| 4,202,816 A | 5/1980 | Moser et al. | |
| 4,205,151 A | 5/1980 | Dale et al. | |
| 4,213,892 A | 7/1980 | Scott | |
| 4,219,453 A | 8/1980 | Sakurai et al. | |
| 4,267,358 A | 5/1981 | Hechenbleikner et al. | |
| 4,281,192 A | 7/1981 | Jacquet et al. | |
| 4,283,572 A | 8/1981 | Klicker | |
| 4,317,933 A | 3/1982 | Parker | |
| 4,341,879 A | 7/1982 | Sugio et al. | |
| 4,355,148 A | 10/1982 | Layer et al. | |
| 4,377,666 A | 3/1983 | Farrar | |
| 4,380,554 A | 4/1983 | Serres, Jr. | |
| 4,447,657 A | 5/1984 | Firth et al. | |
| 4,465,871 A | 8/1984 | Firth et al. | |
| 4,510,296 A | 4/1985 | Hergenrother | |
| 4,511,491 A | 4/1985 | Ishii et al. | |
| 4,634,728 A * | 1/1987 | Dunski et al. .................. 524/219 |
| 4,690,995 A | 9/1987 | Keskey et al. | |
| 4,761,247 A | 8/1988 | Rei et al. | |
| 4,824,929 A | 4/1989 | Arimatsu et al. | |
| 4,849,503 A | 7/1989 | Cotter et al. | |
| 4,855,345 A | 8/1989 | Rosenberger et al. | |
| 4,857,596 A | 8/1989 | MacLeay et al. | |
| 4,870,214 A | 9/1989 | Mina et al. | |
| 4,894,263 A | 1/1990 | Dubois et al. | |
| 4,897,438 A | 1/1990 | Kikuchi et al. | |
| 4,900,671 A | 2/1990 | Pokora et al. | |
| 4,925,591 A | 5/1990 | Nakauchi et al. | |
| 4,968,759 A | 11/1990 | Kikuchi et al. | |
| 4,977,004 A | 12/1990 | Bettle, III et al. | |
| 4,981,917 A | 1/1991 | MacLeay et al. | |

(Continued)

FOREIGN PATENT DOCUMENTS

CS 111291 6/1964

(Continued)

OTHER PUBLICATIONS

Akkara, J.A., et al., "Hematin-Catalyzed Polymerization of Phenol Compounds," *Macromolecules*, 33(7):2377-2382 (2000). Akkara, J.A., et al., "Synthesis and Characterization of Polymers Produced by Horseradish Peroxidase in Dioxane," *J. of Polymer Science: Part A: Polymer Chemistry*, 29(11):1561-1574 (1991).

Armengol, E., et al., "Acid Zeolites as Catalysts in Organic Reactions, *tert*-Butylation of Anthracene, Naphthalene and Thianthrene," *Appl. Catal. A* 149:411-423 (1997).

Ayyagari, M.S., et al., "Controlled Free-Radical Polymerization of Phenol Derivatives by Enzyme-Catalyzed Reactions in Organic Solvents," *Macromolecules*, 28(15): 5192-5197 (1995).

Badamali, S.K., et al., "Influence of Aluminium Sources on the Synthesis and Catalytic Activity of Mesoporous A1MCM-41 Molecular Sieves," *Catal. Today* 63:291-295 (2000).

Belyaev, A., et al., "Structure-Activity Relationship of Diaryl Phosphonate Esters as Potent Irreversible Dipeptidyl Peptidase IV Inhibitors," *J. Med. Chem.*, 42(6):1041-1052 (1998).

(Continued)

*Primary Examiner* — Lorna M Douyon
*Assistant Examiner* — Tanisha Diggs
(74) *Attorney, Agent, or Firm* — Hamilton, Brook, Smith & Reynolds, P.C.

(57) ABSTRACT

Described are antioxidant macromolecules and methods of making and using same.

2 Claims, 3 Drawing Sheets

U.S. PATENT DOCUMENTS

| | | | |
|---|---|---|---|
| 4,994,628 A | 2/1991 | Goddard et al. | |
| 5,013,470 A | 5/1991 | Benfaremo | |
| 5,017,727 A | 5/1991 | Olivier | |
| 5,082,358 A | 1/1992 | Tabata et al. | |
| 5,102,962 A | 4/1992 | Kikuchi et al. | |
| 5,117,063 A | 5/1992 | Stern et al. | |
| 5,143,828 A | 9/1992 | Akkara et al. | |
| 5,155,153 A | 10/1992 | Neri et al. | |
| 5,185,391 A | 2/1993 | Stokich, Jr. | |
| 5,185,407 A | 2/1993 | Wong | |
| 5,188,953 A | 2/1993 | Johnson et al. | |
| 5,191,008 A | 3/1993 | Frost et al. | |
| 5,196,142 A | 3/1993 | Mollet et al. | |
| 5,206,303 A | 4/1993 | Tse et al. | |
| 5,207,939 A | 5/1993 | Farng et al. | |
| 5,274,060 A | 12/1993 | Schadeli | |
| 5,278,055 A | 1/1994 | Cyrus, Jr. et al. | |
| 5,304,589 A | 4/1994 | Davidson et al. | |
| 5,320,889 A | 6/1994 | Bettle, III | |
| 5,449,715 A | 9/1995 | Plochocka et al. | |
| 5,498,809 A | 3/1996 | Emert et al. | |
| RE35,247 E | 5/1996 | Cyrus, Jr. et al. | |
| 5,516,856 A | 5/1996 | Sanchez | |
| 5,541,091 A | 7/1996 | Wheeler et al. | |
| 5,565,300 A | 10/1996 | Uenishi et al. | |
| 5,574,118 A | 11/1996 | Olivier | |
| 5,652,201 A | 7/1997 | Papay et al. | |
| 5,739,341 A | 4/1998 | Dubs et al. | |
| 5,834,544 A | 11/1998 | Lin et al. | |
| 5,837,798 A | 11/1998 | Hutchings et al. | |
| 5,869,592 A | 2/1999 | Gagne et al. | |
| 5,911,937 A | 6/1999 | Hekal | |
| 5,994,498 A | 11/1999 | Tripathy et al. | |
| 6,018,018 A | 1/2000 | Samuelson et al. | |
| 6,046,263 A | 4/2000 | Rasberger et al. | |
| 6,096,695 A | 8/2000 | Lam et al. | |
| 6,096,859 A | 8/2000 | Akkara et al. | |
| 6,150,491 A | 11/2000 | Akkara | |
| 6,232,314 B1 | 5/2001 | Jarrott et al. | |
| 6,342,549 B1 | 1/2002 | Hirose et al. | |
| 6,444,450 B2 | 9/2002 | Akkara et al. | |
| 6,646,035 B2 | 11/2003 | Koch et al. | |
| 6,723,815 B2 | 4/2004 | Callaghan et al. | |
| 6,743,525 B2 | 6/2004 | Bernsten et al. | |
| 6,770,785 B1 | 8/2004 | Desai et al. | |
| 6,794,480 B2 | 9/2004 | Goto et al. | |
| 6,800,228 B1 | 10/2004 | Semen | |
| 6,828,364 B2 | 12/2004 | Gugumus | |
| 7,132,496 B2 | 11/2006 | Kerres et al. | |
| 7,169,844 B2 | 1/2007 | Inokami | |
| 7,205,350 B2 | 4/2007 | Thibaut | |
| 7,223,432 B2 | 5/2007 | Cholli et al. | |
| 7,262,319 B2 | 8/2007 | Rehm et al. | |
| 7,705,176 B2 | 4/2010 | Cholli et al. | |
| 7,705,185 B2 * | 4/2010 | Kumar et al. | 564/414 |
| 2001/0041203 A1 | 11/2001 | Uno et al. | |
| 2002/0007020 A1 | 1/2002 | Higahimura et al. | |
| 2002/0128493 A1 | 9/2002 | Romanczyk, Jr. et al. | |
| 2002/0143025 A1 | 10/2002 | Pratt et al. | |
| 2002/0183470 A1 | 12/2002 | Tripathy et al. | |
| 2003/0030033 A1 | 2/2003 | Duyck et al. | |
| 2003/0078346 A1 | 4/2003 | Nakamura et al. | |
| 2003/0091837 A1 | 5/2003 | Aoki | |
| 2003/0176620 A1 | 9/2003 | Romanczyk, Jr. et al. | |
| 2003/0191242 A1 | 10/2003 | Zedda et al. | |
| 2003/0229196 A1 | 12/2003 | Braat et al. | |
| 2003/0230743 A1 | 12/2003 | Cholli et al. | |
| 2004/0015021 A1 | 1/2004 | Adams et al. | |
| 2004/0164279 A1 | 8/2004 | Stevenson et al. | |
| 2004/0180994 A1 | 9/2004 | Pearson et al. | |
| 2004/0186167 A1 | 9/2004 | Dou et al. | |
| 2004/0186214 A1 | 9/2004 | Li et al. | |
| 2004/0198875 A1 | 10/2004 | Kaprinidis et al. | |
| 2004/0214935 A1 | 10/2004 | Cholli et al. | |
| 2005/0170978 A1 | 8/2005 | Migdal et al. | |
| 2005/0209379 A1 | 9/2005 | Botkin et al. | |
| 2005/0238789 A1 | 10/2005 | Cholli et al. | |
| 2005/0242328 A1 | 11/2005 | Baranski | |
| 2006/0029706 A1 | 2/2006 | Cholli et al. | |
| 2006/0040833 A1 | 2/2006 | Al-Akhdar et al. | |
| 2006/0041087 A1 | 2/2006 | Cholli | |
| 2006/0041094 A1 | 2/2006 | Cholli | |
| 2006/0128929 A1 | 6/2006 | Yang et al. | |
| 2006/0128930 A1 | 6/2006 | Dhawan et al. | |
| 2006/0128931 A1 | 6/2006 | Kumar et al. | |
| 2006/0128939 A1 | 6/2006 | Kumar et al. | |
| 2006/0154818 A1 | 7/2006 | Destro et al. | |
| 2006/0189820 A1 | 8/2006 | Rehm et al. | |
| 2006/0189824 A1 | 8/2006 | Kumar et al. | |
| 2006/0208227 A1 | 9/2006 | Shiraki | |
| 2006/0233741 A1 | 10/2006 | Kumar et al. | |
| 2007/0010632 A1 | 1/2007 | Kaplan et al. | |
| 2007/0106059 A1 | 5/2007 | Cholli et al. | |
| 2007/0135539 A1 | 6/2007 | Cholli et al. | |
| 2007/0149660 A1 | 6/2007 | Kumar et al. | |
| 2007/0154430 A1 | 7/2007 | Cholli et al. | |
| 2007/0154608 A1 | 7/2007 | Cholli et al. | |
| 2007/0154720 A1 | 7/2007 | Cholli et al. | |
| 2007/0161522 A1 | 7/2007 | Cholli et al. | |
| 2008/0249335 A1 | 10/2008 | Cholli et al. | |
| 2008/0293856 A1 | 11/2008 | Kumar et al. | |
| 2008/0311065 A1 | 12/2008 | Cholli | |
| 2009/0184294 A1 | 7/2009 | Cholli et al. | |

FOREIGN PATENT DOCUMENTS

| | | | |
|---|---|---|---|
| DE | 197 47 644 A1 | 5/1999 | |
| DE | 198 43 875 A1 | 3/2000 | |
| EP | 0 181 023 A1 | 5/1986 | |
| EP | 0 289 077 A2 | 11/1988 | |
| EP | 0 358 157 A1 | 3/1990 | |
| EP | 0 404 039 A1 | 12/1990 | |
| EP | 0 618 203 A1 | 10/1994 | |
| EP | 0 688 805 A1 | 12/1995 | |
| EP | 1 067 144 A1 | 1/2001 | |
| EP | 1 468 968 A1 | 10/2004 | |
| FR | 2 183 973 | 1/1974 | |
| GB | 1042639 | 8/1964 | |
| GB | 1 283 103 | 7/1972 | |
| GB | 1 320 169 | 6/1973 | |
| GB | 1 372 042 | 10/1974 | |
| GB | 1 389 442 | 4/1975 | |
| GB | 1 469 245 | 4/1977 | |
| GB | 1 482 649 | 8/1977 | |
| JP | 69002715 B | 1/1966 | |
| JP | 43016392 B4 | 7/1968 | |
| JP | 44024274 | 10/1969 | |
| JP | 44028850 | 11/1969 | |
| JP | 45 2980 | 1/1970 | |
| JP | 49 29339 | 3/1974 | |
| JP | 57085366 A | 5/1982 | |
| JP | 59025814 | 2/1984 | |
| JP | 59197447 | 11/1984 | |
| JP | 60-199832 | 10/1985 | |
| JP | 05 199858 | 8/1993 | |
| JP | 06135876 A | 5/1994 | |
| JP | 06 247959 | 9/1994 | |
| JP | 08027226 A | 1/1996 | |
| JP | 09262069 | 10/1997 | |
| JP | 09 328519 | 12/1997 | |
| JP | 09 328521 | 12/1997 | |
| JP | 9322784 A | 12/1997 | |
| JP | 11-80063 | 3/1999 | |
| JP | 11-158103 | 6/1999 | |
| JP | 2003138258 | 5/2003 | |
| NL | 7 905 000 | 3/1980 | |
| WO | WO 92/20734 | 11/1992 | |
| WO | WO 00/39064 | 7/2000 | |
| WO | WO 01/18125 A1 | 3/2001 | |
| WO | WO 01/48057 A1 | 7/2001 | |
| WO | WO 02/079130 A1 | 10/2002 | |
| WO | WO 03/087260 A1 | 10/2003 | |
| WO | WO 03/102004 A1 | 12/2003 | |
| WO | WO 2004/024070 A2 | 3/2004 | |
| WO | WO 2004/050795 A2 | 6/2004 | |
| WO | WO 2005/025513 A2 | 3/2005 | |
| WO | WO 2005/025646 A2 | 3/2005 | |
| WO | WO 2005/060500 A2 | 7/2005 | |

| | | | |
|---|---|---|---|
| WO | WO 2005/070974 A2 | 8/2005 |
| WO | WO 2005/071005 A1 | 8/2005 |
| WO | WO 2006/018403 A1 | 2/2006 |
| WO | WO 2006/060801 A2 | 6/2006 |
| WO | WO 2006/104957 A2 | 10/2006 |
| WO | WO 2008/005358 A2 | 1/2008 |

OTHER PUBLICATIONS

Blokhin, Y.I, et al., "Phosphorylation of Dihydric Phenols with Amides of Phosphorous Acid," *Russian Chem. Bulletin*, 45(9):2250-2251 (1996).

Bruno, F.F., et al., "Enzymatic Template Synthesis of Polyphenol," Materials Research Society Symposium Proceedings vol. 600, Electroactive Polymers (EAP):255-259 (1999).

Chandra, K.G. and Sharma, M.M., "Alkylation of Phenol with MTBE and Other tert-butyl-ethers:Cation Exchange Resins as Catalysts," *Catal. Lett.* 19(4):309-317 (1993).

Ciric-Marjanovic, et al., Chemical Oxidative Polymerization of Aminodiphenylamines, Journal of Physical Chemistry B, 112, 23: 6976-6987 (2008).

Coppinger, G.B., et al., "Photo-Fries Rearrangement of Aromatic Esters. Role of Steric and Electronic Factors" *J. of Phy. Chem.*, 70(11):3479-3489 (1966).

Database Beilstein [online] Beilstein Institut Zur Förderung Der Chemischen Wissenschaften; XP002420027, Beilstein Registry No. 3517906.

Database Beilstein [online] Beilstein Institut Zur Förderung Der Chemischen Wissenschaften; XP002420028, Beilstein Registry No. 5840042.

Database Beilstein [online] Beilstein Institut Zur Förderung Der Chemischen Wissenschaften; XP002420029, Beilstein Registry No. 2311871.

Database Beilstein [online] Beilstein Institut Zur Förderung Der Chemischen Wissenschaften; XP002420030, Beilstein Registry No. 8876646.

Database Beilstein [online] Beilstein Institut Zur Förderung Der Chemischen Wissenschaften; XP002420031, Beilstein Registry No. 2271400.

Database Beilstein [online] Beilstein Institut Zur Förderung Der Chemischen Wissenschaften; XP002420032, Beilstein Registry No. 2212095.

Database Beilstein [online] Beilstein Institut Zur Förderung Der Chemischen Wissenschaften; XP002420033, Beilstein Registry No. 8941955.

Database Beilstein [online] Beilstein Institut Zur Förderung Der Chemischen Wissenschaften; XP002420034, Database Accession No. 2312425.

Database Beilstein [online] Beilstein Institut Zur Förderung Der Chemischen Wissenschaften; XP002420035, Beilstein Registry No. 905950.

Database Beilstein [online] Beilstein Institut Zur Förderung Der Chemischen Wissenschaften; XP002420036, Beilstein Registry No. 2140308.

Database Beilstein [online] Beilstein Institut Zur Förderung Der Chemischen Wissenschaften; XP002420037, Beilstein Registry No. 134886.

Database Beilstein [online] Beilstein Institut Zur Förderung Der Chemischen Wissenschaften; XP002420038, Beilstein Registry No. 1961007.

Database CA [online] Chemical Abstracts Service, Columbus, Ohio, US, XP-002429584, Database Accession No. 81::153647, Organic Phosphate Stabilizers for Polyamides and Polyurethanes, abstract, Minagawa, M. (1974).

Database Caplus [online] Chemical Abstracts Service, Columbus, Ohio, US, XP-002387095, Database Accession No. 1981:572206, Effectiveness of Inhibitors in the Oxidation of Jet Fuel with an Initiator, abstract, Kovalev, et al.

Devassy, B.M., et al, "Zirconia Supported Phosphotungstic Acid as an Efficient Catalyst for Resorcinol *tert*-Butylation and *n*-Heptane Hydroisomerization," *J. Mol. Catalysis A: Chemical* 221:113-119 (2004).

Ding, et al., "Chemical Trapping Experiments Support a Cation-Radical Mechanism for the Oxidative Polymerization of Aniline," Journal of Polymer Science, Part A: Polymer Chemistry, vol. 37: 2569-2579 (1999).

Dordick, J.S., "Enzymatic Catalysis in Monophasic Organic Solvents," *Enzyme Microb. Technol.*, 11(4):194-211 (1989).

Dordick, J.S., et al., "Polymerization of Phenols Catalyzed by Peroxidase in Nonaqueous Media," *Biotechnology and Bioengineering*, 30(1):31-36 (1987).

English Abstract of Kovalev, G. I., et al., "Study of the Effectiveness of Inhibitors in Oxidation of Jet Fuel in a Closed Volume," *Deposited Doc.*, VINITI: 443-82 (1981).

English Abstract of Kovalev, G.I., et al., "Effectiveness of Inhibitors in the Oxidation of Jet Fuel With an Initiator," *J. Neftekhimiya (Petroleum Chemistry)*, 21(2): 287-298 (1981).

Faber, K., "Biotransformations in Organic Chemistry," A Textbook, Fourth Completely Revised and Extended Edition, Springer-Verlag pp. 347-349 (1953).

FS&T 821 "Antioxidant," [online], [retrieved on Oct. 29, 2002]. Retrieved from the Internet <URL: http://class.fst.ohio-state.edu/fst/lect/aa.pdf.

FS&T 821 "Food Lipids," [online], Oct. 2001 [retrieved on Oct. 29, 2002]. Retrieved from the Internet <URL: http://class.fst.ohio-state.edu/fst821/>.

FST 821 "Course Schedule," [online], [retrieved on Oct. 29, 2002]. Retrieved from the Internet <URL: http://class.fst.ohio-state.edu/fst821/>.

Hatayama, K., et al., "Anti-ulcer Effect of Isoprenyl Flavonoids. III.[1)] Synthesis and Anti-ulcer Activity of Metabolites of 2'-Carboxymethoxly-4,4'-bis(3-methyl-2-butenyloxy)chalcone[2)]," *Chemical & Pharmaceutical Bulletin*, 33(4), 1327-1333(Apr. 1985).

Heidekum, A., et al., "Nafion/Silica Composite Material Reveals High Catalytic Potential in Acylation Reactions," *J. Catal.* 188:230-232 (1999).

Hidalgo, M.E., et al., "Antioxidant Activity of Depsides and Depsidones," Phytochemistry, 37(6):1585-1587 (1994).

Hofer, K., et al., "[[(Anilinooxalyl)amino]phenyl] Phosphite Stabilizers for Polypropylene," Chemical Abstracts Service, ZCAPLUS, document No. 77:62780 (1972).

Ikeda, R., et al., "Novel Synthetic Pathway to a Poly(phenylene oxide). Laccase-Catalyzed Oxidative Polymerization of Syringic Acid," *Macromolecules*, 29:3053-3054 (1996).

International Search Report for related foreign application PCT/US2007/015177, mailed on Jun. 13, 2008.

International Search Report for related foreign application PCT/US2005/044021, mailed on May 22, 2006.

International Search Report for related foreign application PCT/US2005/044022, mailed on May 2, 2006.

International Search Report for related foreign application PCT/US2005/044023, mailed on Nov. 3, 2006.

International Search Report for related foreign application PCT/US2005/044019, mailed on Apr. 28, 2006.

International Search Report for related foreign application PCT/US2005/025646, mailed on Mar. 13, 2006.

International Search Report for related foreign application PCT/US2005/025513, mailed on Mar. 13, 2006.

International Search Report for related foreign application PCT/US2006/006355, mailed on Jul. 31, 2006.

International Search Report for related foreign application PCT/US2006/010985, mailed on Dec. 19. 2006.

International Search Report for related foreign application PCT/US2006/042240, mailed on May 3, 2007.

International Search Report for related foreign application PCT/US2006/042235, mailed on Apr. 27, 2007.

International Search Report for related foreign application PCT/US2006/045929, mailed on Apr. 20, 2007.

Ismail, M.N. and Wazzan, A.A., "Evaluation of New Thermal Stabilizers and Antifatigue Agents for Rubber Vulcanizates," *Polymer-Plastics Tech. and Eng.*, 45:751-758 (2006).

Jayaprakasha, G.K., et al., "Antioxidant Activity of Grape Seed (*Vitis vinifera*) Extracts on Peroxidation Models in vitro," *Food Chemistry*, 73:285-290 (2001).

Jialanella, G.and Pilrma, I., "Synthesis of Poly(vinyl alcohol-co-vinyl gallate) by the Chemical Modification of Poly(vinyl alcohol)," Polymer Bulletin 18:385-389 (1987).

Joossens, J., et al., "Diphenyl Phosphonate Inhibitors for the Urokinase-Type Plasminogen Activator: Optimization of the P4 Position," *J. Med. Chem.*, 49:5785-5793 (2006).

Kamitori, Y., et al., "Silica Gel as an Effective Catalyst for the Alkylation of Phenols and Some Heterocylic Aromatic Compounds," *J. Org. Chem.* 49: 4161-4165 (1984).

Kazandjian, R.Z., et al., "Enzymatic Analyses in Organic Solvents," *Biotechnology and Bioengineering*, XXVIII:417-421 (1986).

Khan, K.M., et al., "An Expedient Esterification of Aromatic Carboxylic Acids Using Sodium Bromate and Sodium Hydrogen Sulfite," *Tetrahedron* 59(29):5549-5554 (2003).

Kim, T. H., et al., "Melt Free-Radical Grafting of Hindered Phenol Antioxidant onto Polyethylene," *J. Applied Polymer Science*, 77:2968-2973 (2000).

Klibanov, A.M., et al., "Enzymatic Removal of Toxic Phenols and Anilines from Waste Waters," *J. of Applied Biochemistry*, 2(5):414-421 (1980).

Koshchii, V.A., et al. "Alkylation of Phenol by Alcohols in the Presence of Alumium Phenolate," *Org. Chem.* 24(7):1358-1361 (1988).

Lalancette, J.M., et al. "Metals Intercalated in Graphite. II. The Friedel-Crafts Reactions with $ALCL_3$-Graphite," *Can. J. Chem.* 52:589-591 (1974).

Li, et al., "Novel Multifunctional Polymers from Aromatic Diamines by Oxidative Polymerizations," Chemical Reviews, vol. 102(9): pp. 2925-2943 (2002).

Maki, M., et al., "Weather-Resistant Colored Polypropylene," Chemical Abstracts Service, ZCAPLUS, document No. 89:111364 (1978).

March, J., Advanced Organic Chemistry, McGraw Hill Book Company, New York, pp. 251-259 (1977).

Masada, H. and Oishi, Y., "A New Synthesis of aryl *t*-butyl Ethers," *Chem. Letters*, 57-58 (1978).

Masada, H. et al., "A New Heterogeneous Williamson Synthesis of Ethers Using *t*-alkyl Substrates," the *Chemical Society of Japan* 3:275-282 (1996).

Masada, H., et al., "A New Method for the Williamson Ether Synthesis Using *t*-alkyl Halides in Nonpolar Solvents," *The Chemical Society of Japan*, 2:164-166 (1995).

Mehdipour-Ataei, S., et al., "Novel Diols Containing Ester and Amide Groups and Resulting Poly(ester amide ester)s," *J. Applied Polymer Sci.*, 93:2699-2703 (2004), XP002420014.

Mejias, L., et al. "New Polymers From Natural Phenols Using Horseradish or Soybean Peroxidase," *Macromol. Biosci.*, 2:24-32 (2002).

Ol'dekop, Yu. A., et al. "Simple Synthesis of the tert-butyl Ether of Phenol" Inst. Fiz-Org. Khim., Minsk, USSR. *Zhurnal Obshchei Khimii*, 50(2):475-6 (1980).

Overgaag, M., et al., "Rearrangement of Alkyl Phenyl Ethers Over Dealuminated HY Zeolites Under Liquid-Phase Conditions," *Applied Catalysis A: General, Elsevier Sci.*, 175(1-2):139-146 (1998).

Pätoprstý, V., et al., "$^{13}$C NMR Study of 3,9-Di(alkylphenoxy)-2,4,8,10-tetraoxa-3,9-diphosphaspiro[5.5]undecanes," *Magnetic Resonance in Chem*, 23(2):122-126 (1985).

Pirozhenko, V.V., et al., "NMR Study of Topomerization of *N*-Aroyl-*p*-Benzoquinonemonoimines," *Russian J. of Organic Chem.*, 31(11):1514-1519 (1995).

Quaschning, V., et al., "Properties of Modified Zirconia Used as Friedel-Crafts-Acylation Catalysts," *J. Catal.* 177:164-174 (1998).

Ryu, K., et al., "Peroxidase-Catalyzed Polymerization of Phenols," Biocatalysis in Agricultural Biotechnology, Chapter 10:141-157 (1988).

Sakthivel, A., et al., "Vapour Phase Tertiary Butylation of Phenol Over Sulfated Zirconia Catalyst," *Catal. Lett.*, 72(3-4):225-228 (2001).

Sartori G., et al., "Highly Selective Mono-*tert*-butylation of Aromatic Compounds," *Chem. Ind.*, (London), (22):762-763 (1985).

Scharpe, S.L., et al., "Serine Peptidase Modulators, Their Preparation, and Their Therapeutic Use," Chemical Abstracts Service, ZCAPLUS, document No. 131:223514 (1999).

Notification Concerning Transmittal of International Preliminary Report and Written Opinion of the International Searching Authority, or the Declaration for application PCT/US2006/042251, mailed on Feb. 22, 2007.

RN 85650-63-1, 1984.

Singh, A. and Kaplan, D. L., "Biocatalytic Route to Ascorbic Acid-Modified Polymers for Free-Radical Scavenging," *Adv. Matter.*, 15(15):1291-1294 (2003).

Spano, R., et al., "Substituted Anilides of 3-Monoethyl Ester of 4 Hydroxyisophthalic Acid," *J. of Med. Chem.*, 15(5):552-553 (1971).

Thompson, C. Ray, "Stability of Carotene in Alfalfa Meal: Effect of Antioxidants," *Industrial & Engineering Chemistry*, 24(5): 922-925 (1950).

Tsvetkov, O.N., et al., "Alkylation of Phenols with Higher Olefins. Part I," *Int. Chem. Eng.* 7(1):104-121 (1967).

XP-002419239, "Discover Our World of Effects for Polyolefins," *Ciba Speciality Chemicals*, (2003).

Notification of Transmittal of the International Search Report and the Written Opinion of the International Searching Authority, or the Declaration for related foreign application PCT/US2007/015177, mailed on Jun. 13, 2008.

Notification Concerning Transmittal of International Preliminary Report on Patentability for related foreign application PCT/US2007/015177, mailed on Jan. 15, 2009.

Al-Malaika, S and Suharty, N., "Reactive Processing of Polymers: Mechanisms of Grafting Reactions of Functional Antioxidants on Polyolefins in the Presence of a Coagent," Polymer Degradation and Stability 49: 77-89 (1995).

Notification Concerning Transmittal of International Preliminary Report on Patentability for application PCT/US2006/042251, mailed on May 8, 2008.

Written Opinion for related foreign application PCT/US2005/025646, mailed on Nov. 14, 2006.

Notification Concerning Transmittal of International Preliminary Report on Patentability for related foreign application PCT/US2005/025646, mailed on Dec. 20, 2006.

Office Action for related foreign application EP05773305.7 dated Apr. 24, 2008.

Examiner's Report No. 1 for related foreign application AU 2005269754 dated Apr. 1, 2008.

Examiner's Report No. 1 for related foreign application AU 2005269780 dated Apr. 2, 2008.

Examiner's Report No. 2 for related foreign application AU 2005269754 dated Jan. 5, 2010.

Examiner's Report No. 3 for related foreign application AU 2005269754 dated Jan. 12, 2010.

Preliminary Report on Patentability and Written Opinion for related foreign application PCT/US2005/025513, issued Jan. 23, 2007.

Office Action for related foreign application EP06720996.5-2103 dated Mar. 23, 2009.

Office Action for related foreign application EP06720996.5-2103 dated Apr. 21, 2008.

International Preliminary Report on Patentability for PCT/US2005/001946, issued Jul. 24, 2006.

* cited by examiner

MACROMOLECULAR ANTIOXIDANTS COMPRISING DIFFERING ANTIOXIDANT MOIETIES: STRUCTURES, METHODS OF MAKING AND USING THE SAME

RELATED APPLICATIONS

This application is a continuation of International Application No. PCT/US2007/015177, which designated the United States and was filed on Jun. 29, 2007, published in English, which claims the benefit of U.S. Provisional Application No. 60/818,876, filed on Jul. 6, 2006. The entire teachings of the above applications are incorporated herein by reference.

BACKGROUND OF THE INVENTION

Antioxidants are employed to prevent oxidation in a wide range of materials, for example, plastics, elastomers, lubricants, petroleum based products (lubricants, gasoline, aviation fuels, and engine oils), cooking oil, cosmetics, processed food products, and the like. While many antioxidants exist, there is a continuing need for new antioxidants that have improved properties.

SUMMARY OF THE INVENTION

The present invention relates to antioxidant macromolecules that in general have improved antioxidant properties.

In one embodiment the present invention is directed to compounds represented Structural Formula I or II:

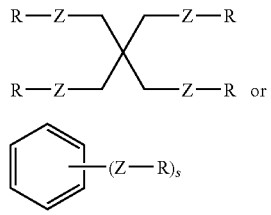

wherein:
R is:

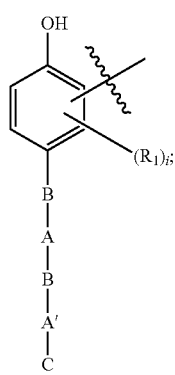

A in each occurrence, independently is —O—, —NH—, —S—, —C(O)—, —C(O)NH—, —NHC(O)—, —C(O)O—, —OC(O)—, —CH=N— or —N=CH—;

A' in each occurrence, independently is a bond, —O—, —NH—, —S—, —C(O)—, —C(O)NH—, —NHC(O)—, —C(O)O—, —OC(O)—, —CH=N— or —N=CH—;

B in each occurrence, independently is a bond or an optionally substituted alkylene group;

C in each occurrence independently is —H, an optionally substituted alkylene group or

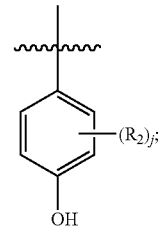

$R_1$ and $R_2$ in each occurrence, independently is an optionally substituted alkyl, optionally substituted aryl or optionally substituted aralkyl;

Z in each occurrence, independently is a bond, an optionally substituted alkylene group, —$(CH_2)_l$NHC(O)$(CH_2)_l$—, —$(CH_2)_l$C(O)NH$(CH_2)_l$—, —$(CH_2)_l$C(O)O$(CH_2)_l$—, —$(CH_2)_l$OC(O)$(CH_2)_l$—, —$(CH_2)_l$CH=N$(CH_2)_l$—, —$(CH_2)_l$N=CH$(CH_2)_l$—, —$(CH_2)_l$NH$(CH_2)_l$—, —$(CH_2)_l$S$(CH_2)_l$—, —$(CH_2)_l$O$(CH_2)_l$— or —$(CH_2)_l$C(O)$(CH_2)_l$—;

i in each occurrence, independently is 0, 1, 2 or 3;
j in each occurrence, independently is 0, 1, 2, 3 or 4;
l in each occurrence, independently is 0 or a positive integer from 1 to 12; and
s is a positive integer from 1 to 6.

In another embodiment the present invention is directed to compounds represented Structural Formula III or IV:

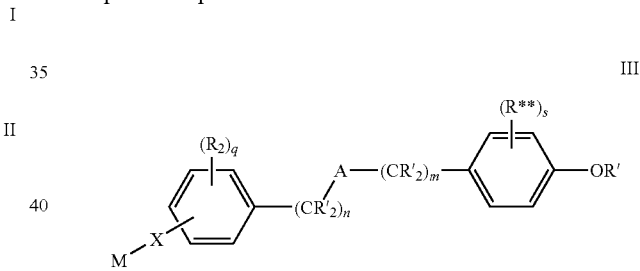

wherein:
A is —C(O)NR'—, —NR'C(O)—, —NR'—, —CR'=N—, —C(O)—, —C(O)O—, —OC(O)—, —O—, —S—, —C(O)OC(O)— or a bond;

each R' is independently —H or optionally substituted alkyl;

each R** is independently an optionally substituted alkyl, optionally substituted aryl, optionally substituted alkoxycarbonyl, optionally substituted ester, —OH, —NH$_2$,

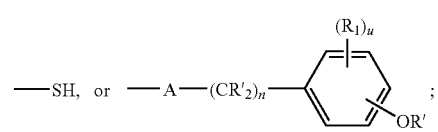

each $R_1$ and $R_2$ is independently an optionally substituted alkyl, optionally substituted aryl, optionally substituted alkoxycarbonyl, optionally substituted ester, —OH, —NH$_2$ or —SH;

X is —C(O)O—, —OC(O)—, —C(O)NR'—, —NR'C(O)—, —NR'—, —CH=N—, —C(O)—, —O—, —S—, —NR'— or —C(O)OC(O)—;

M is —H, an alkyl or

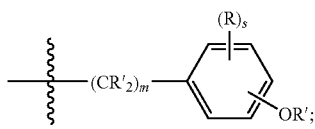

each n is independently a positive integer from 1 to 6;
each m is independently 0 or a positive integer from 1 to 6; and
each s, q and u are independently integers from 0 to 4.

wherein R is:

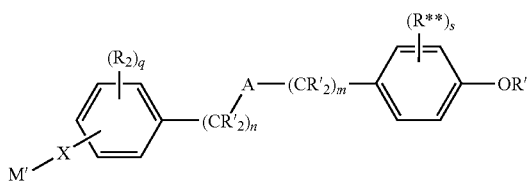

A is —C(O)NR'—, —NR'C(O)—, —NR'—, —CR'=N—, —C(O)—, —C(O)O—, —OC(O)—, —O—, —S—, —C(O)OC(O)— or a bond;

Z in each occurrence, independently is a bond, an optionally substituted alkylene group, —(CH$_2$)$_l$NHC(O)(CH$_2$)$_l$—, —(CH$_2$)$_l$C(O)NH(CH$_2$)$_l$—, —(CH$_2$)$_l$C(O)O(CH$_2$)$_l$—, —(CH$_2$)$_l$OC(O)(CH$_2$)$_l$—, —(CH$_2$)$_l$CH=N(CH$_2$)$_l$—, —(CH$_2$)$_l$N=CH(CH$_2$)$_l$—, —(CH$_2$)$_l$NH(CH$_2$)$_l$—, —(CH$_2$)$_l$S(CH$_2$)$_l$—, —(CH$_2$)$_l$—O(CH$_2$)$_l$— or —(CH$_2$)$_l$C(O)(CH$_2$)$_l$—;

each R' is independently —H or optionally substituted alkyl;

each R** is independently an optionally substituted alkyl, optionally substituted aryl, optionally substituted alkoxycarbonyl, optionally substituted ester, —OH, —NH$_2$, —SH, or

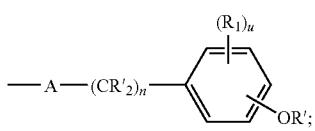

each R$_1$ and R$_2$ is independently an optionally substituted alkyl, optionally substituted aryl, optionally substituted alkoxycarbonyl, optionally substituted ester, —OH, —NH$_2$ or —SH;

X is —C(O)O—, —OC(O)—, —C(O)NR'—, —NR'C(O)—, —NR'—, —CR'=N—, —C(O)—, —O—, —S—, —NR'— or —C(O)OC(O)—;

each M' is independently —H, alkyl, or

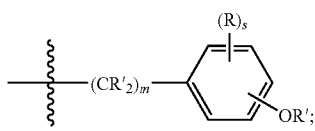

each n is independently a positive integer from 1 to 6;
each m is independently 0 or a positive integer from 1 to 6;

l in each occurrence, independently is 0 or a positive integer from 1 to 12; and
k in each occurrence independently is a positive integer from 1 to 12;
each q is independently an integer from 0 to 3;
each s, and u are independently integers from 0 to 4; and
r is an integer from 0 to 4.

In another embodiment the present invention is directed to methods of inhibiting oxidation in an oxidizable material comprising combining the oxidizable material with a compound described herein.

In another embodiment the present invention is directed to methods of inhibiting oxidation in an oxidizable material comprising combining the oxidizable material with a composition comprising a compound described herein.

In another embodiment the present invention is a method of making a compound described herein.

In certain embodiments, the antioxidant macromolecules of the present invention can have enhanced antioxidant activity and better thermal stability compared to commercially available antioxidants.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1:
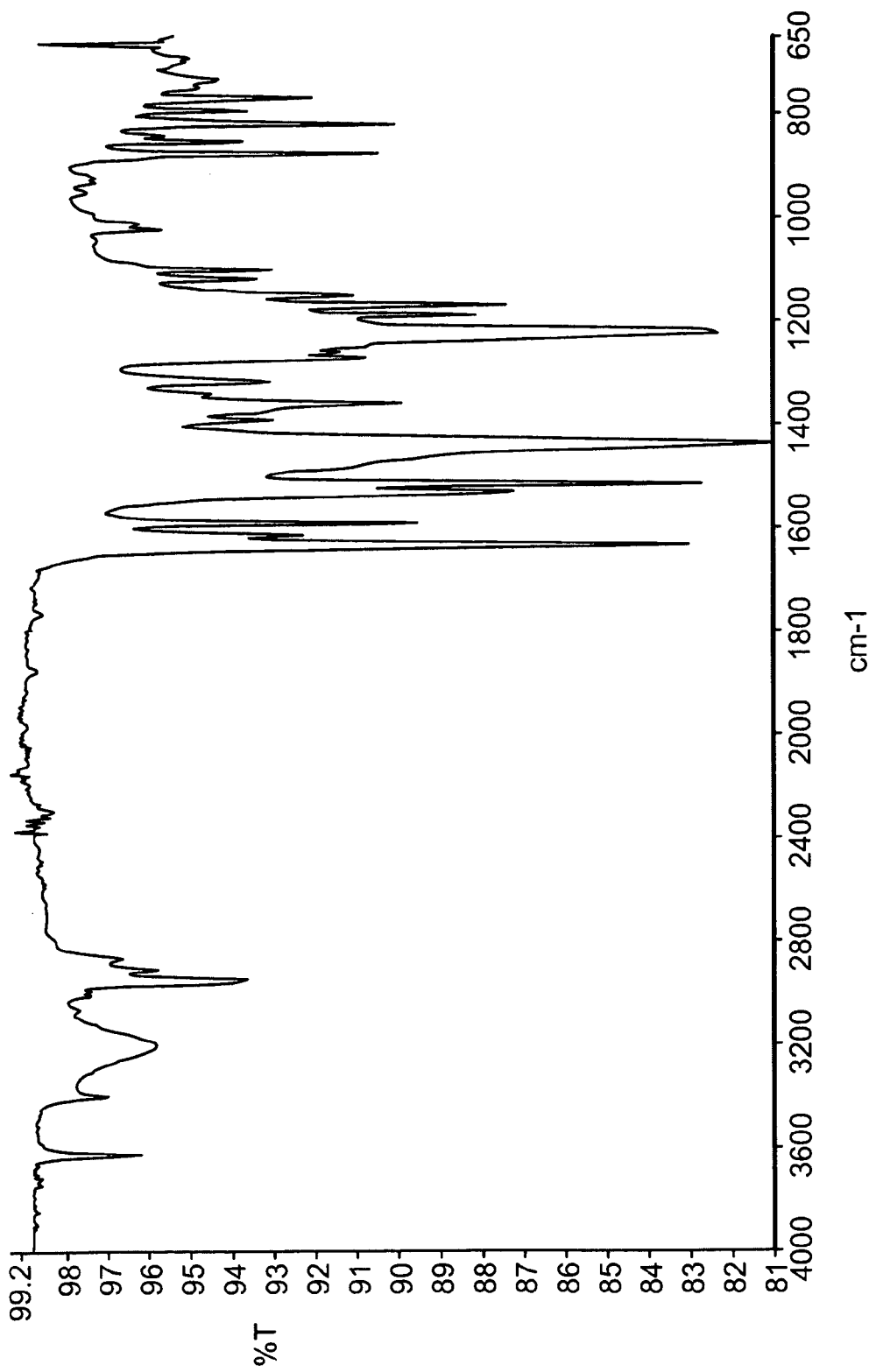
FIG. 1 is an IR spectrum of a tyramine based product of the present invention.

A description of preferred embodiments of the invention follows.

In certain embodiments the compounds of the present invention comprise at least one sterically hindered groups such as phenol groups (antioxidant moiety). Sterically hindered, as used herein means that the substituent group (e.g., bulky alkyl group) on a ring carbon atom adjacent (or alternatively para) to a ring carbon atom substituted with a phenolic hydroxy group (or thiol or amine group), is large enough to sterically hinder the phenolic hydroxy group (or thiol or amine groups). This steric hindrance, in certain embodiments results in more labile or weak bonding between the oxygen and the hydrogen (or sulfur or nitrogen and hydrogen) and in turn enhances the stability and antioxidant activity (proton donating activity) of the sterically hindered antioxidant.

Repeat units of the antioxidants of the invention include substituted benzene molecules. Some of these benzene molecules are typically based on phenol or a phenol derivative, such that they have at least one hydroxyl or ether functional group. In certain embodiments, the benzene molecules have a hydroxyl group. The hydroxyl group can be a free hydroxyl group and can be protected or have a cleavable group attached to it (e.g., an ester group). Such cleavable groups can be released under certain conditions (e.g., changes in pH), with a desired shelf life or with a time-controlled release (e.g., measured by the half-life), which allows one to control where and/or when an antioxidant can exert its antioxidant effect. The repeat units can also include analogous thiophenol and aniline derivatives, e.g., where the phenol —OH can be replaced by —SH, —NH—, and the like.

Substituted benzene repeat units of an antioxidant of the invention are also typically substituted with a bulky alkyl group or an n-alkoxycarbonyl group. In certain embodiments, the benzene monomers are substituted with a bulky alkyl group. In certain other embodiments, the bulky alkyl group is located ortho or meta to a hydroxyl group on the benzene ring, typically ortho. A "bulky alkyl group" is defined herein as an alkyl group that is branched alpha- or beta- to the benzene ring. In certain other embodiments, the alkyl group is branched alpha to the benzene ring. In certain other embodiments, the alkyl group is branched twice alpha to the benzene ring, such as in a tert-butyl group. Other examples of bulky alkyl groups include isopropyl, 2-butyl, 3-pentyl, 1,1-dimethylpropyl, 1-ethyl-1-methylpropyl and 1,1-diethylpropyl. In certain other embodiments, the bulky alkyl groups are unsubstituted, but they can be substituted with a functional group that does not interfere with the antioxidant activity of the molecule. Straight chained alkoxyl carbonyl groups include methoxycarbonyl, ethoxycarbonyl, n-propoxycarbonyl, n-butoxycarbonyl and n-pentoxycarbonyl. N-propoxycarbonyl is a preferred group. Similar to the bulky alkyl groups, n-alkoxycarbonyl groups are optionally substituted with a functional group that does not interfere with the antioxidant activity of the molecule.

In certain embodiments for compounds represented by Structural Formula I or II or narrower embodiments thereof:

R is:

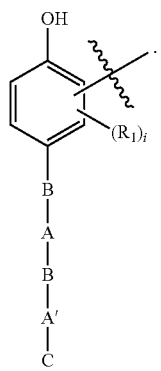

In other embodiments, R is:

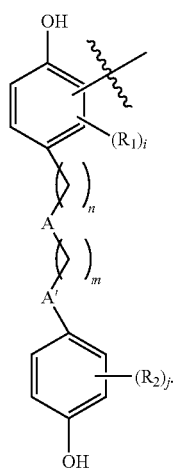

In other embodiments, R is:

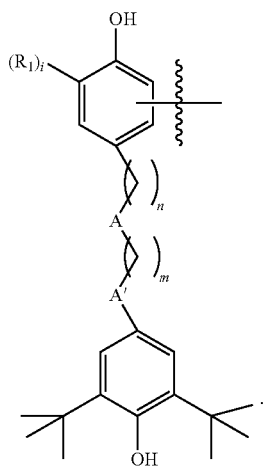

In other embodiments, R is:

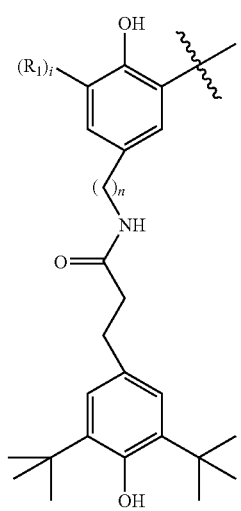

In other embodiments, R is:

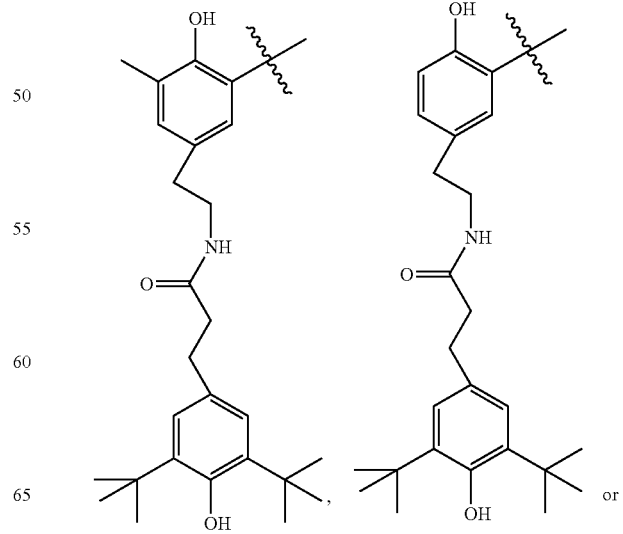

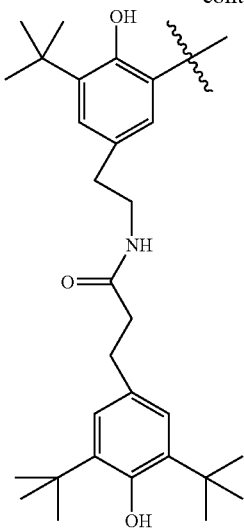

A in each occurrence, independently is —O—, —NH—, —S—, —C(O)—, —C(O)NH—, —NHC(O)—, —C(O)O—, —OC(O)—, —CH=N— or —N=CH—. In other embodiments, A in each occurrence, independently is —C(O)O— or —OC(O)—. In other embodiments A in each occurrence, independently is —C(O)NH— or —NHC(O)—;

A' in each occurrence, independently is a bond, —O—, —NH—, —S—, —C(O)—, —C(O)NH—, —NHC(O)—, —C(O)O—, —OC(O)—, —CH=N— or —N=CH—. In other embodiments, A' is a bond;

B in each occurrence, independently is a bond or an optionally substituted alkylene group. In certain embodiments both B groups are a C2 alkylene group. In certain embodiments one B groups is a C2 alkylene group, and the other is a bond;

C in each occurrence independently is —H, an optionally substituted alkylene group or

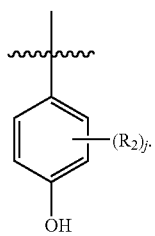

In certain embodiments C is a sterically hindered antioxidant moiety represented by the following structural formula:

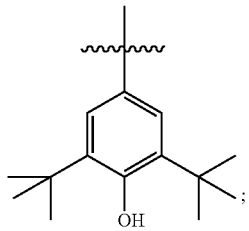

$R_1$ and $R_2$ in each occurrence, independently is an optionally substituted alkyl, optionally substituted aryl or optionally substituted aralkyl. In other embodiments, $R_1$ and $R_2$ in each occurrence, independently is an optionally substituted alkyl. In other embodiments, $R_1$ is a C1-C6 alkyl. In other embodiments $R_1$ is a tert-butyl;

Z in each occurrence, independently is a bond, an optionally substituted alkylene group, —$(CH_2)_i$NHC(O)$(CH_2)_l$—, —$(CH_2)_i$C(O)NH$(CH_2)_l$—, —$(CH_2)_i$C(O)O$(CH_2)_l$—, —$(CH_2)_i$OC(O)$(CH_2)_l$—, —$(CH_2)_i$CH=N$(CH_2)_l$—, —$(CH_2)_i$N=CH$(CH_2)_l$—, —$(CH_2)_i$NH$(CH_2)_l$—, —$(CH_2)_i$S$(CH_2)_l$—, —$(CH_2)_i$O$(CH_2)_l$— or —$(CH_2)_i$C(O)$(CH_2)_l$—. In other embodiments, Z in each occurrence, independently is a bond, an optionally substituted alkylene group, —$(CH_2)_i$NHC(O)$(CH_2)_l$—, —$(CH_2)_i$C(O)NH$(CH_2)_l$—, —$(CH_2)_i$C(O)O$(CH_2)_l$—, —$(CH_2)_i$OC(O)$(CH_2)_l$—, —$(CH_2)_i$O$(CH_2)_l$— or —$(CH_2)_i$C(O)$(CH_2)_l$—. In other embodiments, Z in each occurrence, independently is a bond, an optionally substituted alkylene group, —$(CH_2)_i$C(O)O$(CH_2)_l$—, —$(CH_2)_i$OC(O)$(CH_2)_l$—, —$(CH_2)_i$O$(CH_2)_l$— or —$(CH_2)_i$C(O)$(CH_2)_l$—. In other embodiments, Z in each occurrence, independently is —$(CH_2)_i$C(O)O$(CH_2)_l$— or —$(CH_2)_i$OC(O)$(CH_2)_l$—. In other embodiments, Z is —$(CH_2)_i$O$(CH_2)_l$—. In other embodiments, Z is —$(CH_2)_i$C(O)$(CH_2)_l$—;

i in each occurrence, independently is 0, 1, 2 or 3. In other embodiments, i in each occurrence, independently is 0, 1, or 2. In other embodiments, i is 0 or 1;

j in each occurrence, independently is 0, 1, 2, 3 or 4. In other embodiments, j in each occurrence, independently is 0, 1 or 2. In other embodiments j is 2.

l in each occurrence, independently is 0 or a positive integer from 1 to 12. In other embodiments, l in each occurrence independently is 0 or a positive integer from 1 to 6. In other embodiments l in each occurrence independently is 0 or a positive integer from 1 to 3;

s is a positive integer from 1 to 6. In other embodiments, s is 3; and n and m in each occurrence, independently is 0 or a positive integer from 1 to 12. In other embodiments, n and m in each occurrence, independently is 0 or a positive an integer from 1 to 6. In other embodiments, n is an integer from 0 to 4. In other embodiments both n and m are 2. In other embodiments n is 0 and m is 2.

In certain embodiments of the present invention the compound is represented by structural formula I.

In certain embodiments of the present invention the compound is represented by structural formula II. In certain embodiments of the present invention structural formula II is represented by the following structural formula:

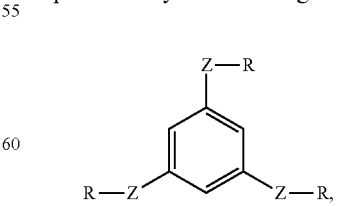

and the remainder of the variables are as described above.

In a first embodiment for compounds of Structural formula I and II:

R is:

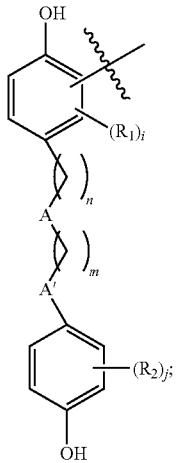

wherein:
n and m in each occurrence, independently is 0 or a positive integer from 1 to 12; and the remainder of the variables are as described above.

In a second embodiment for compounds of Structural formula I and II:
$R_1$ and $R_2$ in each occurrence, independently is an optionally substituted alkyl; and
i and j in each occurrence, independently is 0, 1 or 2 and the remainder of the variables are as described above in the first embodiment.

In a third embodiment for compounds of Structural formula I and II:
R is:

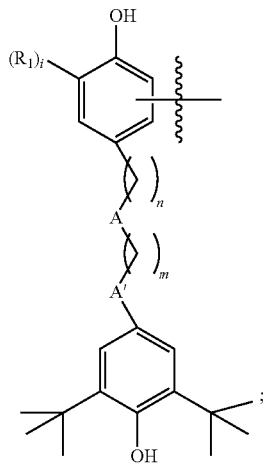

wherein:
n and m in each occurrence, independently is 0 or a positive an integer from 1 to 6; and
i is 0 or 1 and the remainder of the variables are as described above in the second embodiment.

In a fourth embodiment for compounds of Structural formula I and II:
Z in each occurrence, independently is a bond, an optionally substituted alkylene group, —(CH$_2$)$_l$NHC(O)(CH$_2$)$_l$—, —(CH$_2$)$_l$C(O)NH(CH$_2$)$_l$—, —(CH$_2$)$_l$C(O)O(CH$_2$)$_l$—, —(CH$_2$)$_l$OC(O)(CH$_2$)$_l$—, —(CH$_2$)$_l$O(CH$_2$)$_l$— or —(CH$_2$)$_l$C(O)(CH$_2$)$_l$—; and
l in each occurrence independently is 0 or a positive integer from 1 to 6 and the remainder of the variables are as described above in the third embodiment.

In a fifth embodiment for compounds of Structural formula I and II:
A in each occurrence, independently is —C(O)O— or —OC(O)— and the remainder of the variables are as described above in the fourth embodiment.

Alternatively, A in each occurrence, independently is —C(O)NH— or —NHC(O)— and the remainder of the variables are as described above in the fourth embodiment.

In a sixth embodiment for compounds of Structural formula I and II:
R is:

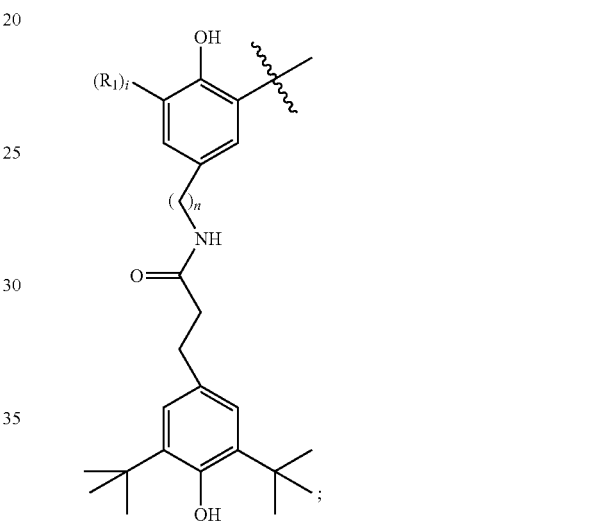

wherein:
n is an integer from 0 to 4; and
$R_1$ is a C1-C6 alkyl and the remainder of the variables are as described above in the fifth embodiment.

In a seventh embodiment for compounds of Structural formula I and II:
Z in each occurrence, independently is a bond, an optionally substituted alkylene group, —(CH$_2$)$_l$C(O)O(CH$_2$)$_l$—, —(CH$_2$)$_l$OC(O)(CH$_2$)$_l$—, —(CH$_2$)$_l$O(CH$_2$)$_l$— or —(CH$_2$)$_l$C(O)(CH$_2$)$_l$—; and
l in each occurrence independently is 0 or a positive integer from 1 to 3

In certain embodiments for compounds represented by Structural Formula III or IV or narrower embodiments thereof:
A is —C(O)NR'—, —NR'C(O)—, —NR'—, —CR'=N—, —C(O)—, —C(O)O—, —OC(O)—, —O—, —S—, —C(O)OC(O)— or a bond. In other embodiments, A is —C(O)O—, —OC(O)—, —C(O)NH—, —NHC(O)—, —NH—, —O— or —C(O)—. In other embodiments, A is —C(O)NH— or —NHC(O)—. In certain embodiments, A is not —C(O)O—, —OC(O)—, —O— or —NH—. In various embodiments, A is —OC(O)—. In another embodiment, A is —C(O)O—. In another embodiment, A is —C(O)NH—. In another embodiment, A is —NHC(O)—. In another embodiment, A is —NH—. In another embodiment, A is —CH=N—. In another embodiment, A is —C(O)—. In another embodiment, Z is —O—. In another embodiment, A is —C(O)OC(O)—. In another embodiment, A is a bond;

Z in each occurrence, independently is a bond, an optionally substituted alkylene group, —(CH$_2$)$_t$NHC(O)(CH$_2$)$_t$—, —(CH$_2$)$_t$C(O)NH(CH$_2$)$_t$—, —(CH$_2$)$_t$C(O)O(CH$_2$)$_t$—, —(CH$_2$)$_t$OC(O)(CH$_2$)$_t$—, —(CH$_2$)$_t$CH=N(CH$_2$)$_t$—, —(CH$_2$)$_t$N=CH(CH$_2$)$_t$—, —(CH$_2$)$_t$NH(CH$_2$)$_t$—, —(CH$_2$)$_t$S(CH$_2$)$_t$—, —(CH$_2$)$_t$O(CH$_2$)$_t$— or —(CH$_2$)$_t$C(O)(CH$_2$)$_t$—. In other embodiments, Z in each occurrence, independently is a bond, an optionally substituted alkylene group, —(CH$_2$)$_t$NHC(O)(CH$_2$)$_t$—, —(CH$_2$)$_t$C(O)NH(CH$_2$)$_t$—, —(CH$_2$)$_t$C(O)O(CH$_2$)$_t$—, —(CH$_2$)$_t$OC(O)(CH$_2$)$_t$—, —(CH$_2$)$_t$—O(CH$_2$)$_t$— or —(CH$_2$)$_t$C(O)(CH$_2$)$_t$—. In other embodiments, Z in each occurrence, independently is a bond, an optionally substituted alkylene group, —(CH$_2$)$_t$C(O)O(CH$_2$)$_t$—, —(CH$_2$)$_t$OC(O)(CH$_2$)$_t$—, —(CH$_2$)$_t$O(CH$_2$)$_t$— or —(CH$_2$)$_t$C(O)(CH$_2$)$_t$—. In other embodiments, Z in each occurrence, independently is —(CH$_2$)$_t$C(O)O(CH$_2$)$_t$— or —(CH$_2$)$_t$OC(O)(CH$_2$)$_t$—. In other embodiments, Z is —(CH$_2$)$_t$O(CH$_2$)$_t$—. In other embodiments, Z is —(CH$_2$)$_t$C(O)(CH$_2$)$_t$—;

Each R' is independently —H or optionally substituted alkyl. In certain other embodiments R' is —H or an alkyl group. In certain other embodiments R' is —H or a C1-C10 alkyl group. In certain other embodiments R' is —H.

Each R is independently an optionally substituted alkyl, optionally substituted aryl, optionally substituted alkoxycarbonyl, optionally substituted ester, —OH, —NH$_2$, —SH, or

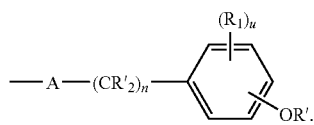

In certain other embodiments, each R is independently an optionally substituted alkyl or optionally substituted alkoxycarbonyl. In certain other embodiment each R is independently an alkyl or alkoxycarbonyl. In certain other embodiments each R is independently a C1-C6 alkyl or a C1-C6 alkoxycarbonyl. In certain other embodiments each R is independently tert-butyl or propoxycarbonyl. In certain other embodiments each R is independently an alkyl group. In certain embodiments each R is independently a bulky alkyl group. Suitable examples of bulky alkyl groups include butyl, sec-butyl, tert-butyl, 2-propyl, 1,1-dimethylhexyl, and the like. In certain embodiments each R is tert-butyl. In certain embodiments at least one R adjacent to the —OH group is a bulky alkyl group (e.g., butyl, sec-butyl, tert-butyl, 2-propyl, 1,1-dimethylhexyl, and the like). In certain other embodiments both R groups adjacent to —OH are bulky alkyl groups (e.g., butyl, sec-butyl, tert-butyl, 2-propyl, 1,1-dimethylhexyl, and the like). In another embodiment, both R groups are tert-butyl. In another embodiment, both R groups are tert-butyl adjacent to the OH group.

Each R$_1$ is independently an optionally substituted alkyl, optionally substituted aryl, optionally substituted alkoxycarbonyl, optionally substituted ester, —OH, —NH$_2$ or —SH. In certain other embodiments, each R$_1$ is independently an optionally substituted alkyl or optionally substituted alkoxycarbonyl. In certain other embodiment each R$_1$ is independently an alkyl or alkoxycarbonyl. In certain other embodiments each R$_1$ is independently a C1-C6 alkyl or a C1-C6 alkoxycarbonyl. In certain other embodiments each R$_1$ is independently tert-butyl or propoxycarbonyl. In certain other embodiments each R$_1$ is independently an alkyl group. In certain embodiments each R$_1$ is independently a bulky alkyl group. Suitable examples of bulky alkyl groups include butyl, sec-butyl, tert-butyl, 2-propyl, 1,1-dimethylhexyl, and the like. In certain embodiments each R$_1$ is tert-butyl. In certain embodiments at least one R$_1$ adjacent to the —OH group is a bulky alkyl group (e.g., butyl, sec-butyl, tert-butyl, 2-propyl, 1,1-dimethylhexyl, and the like). In certain other embodiments both R$_1$ groups adjacent to —OH are bulky alkyl groups (e.g., butyl, sec-butyl, tert-butyl, 2-propyl, 1,1-dimethylhexyl, and the like). In another embodiment, both R$_1$ groups are tert-butyl. In another embodiment, both R$_1$ groups are tert-butyl adjacent to the OH group.

Each R$_2$ is independently an optionally substituted alkyl, optionally substituted aryl, optionally substituted alkoxycarbonyl, optionally substituted ester, —OH, —NH$_2$ or —SH. In certain other embodiments, each R$_2$ is independently an optionally substituted alkyl or optionally substituted alkoxycarbonyl. In certain other embodiment each R$_2$ is independently an alkyl or alkoxycarbonyl. In certain other embodiments, each R$_2$ is independently an optionally substituted alkyl. In certain other embodiment each R$_2$ is independently an alkyl. In certain other embodiments each R$_2$ is independently a C1-C10 alkyl. In certain other embodiments each R$_2$ is independently a C1-C6 alkyl. In certain other embodiments each R$_2$ is independently a bulky alkyl group or a straight chained alkyl group. In certain other embodiments each R$_2$ is independently methyl, ethyl, propyl, butyl, sec-butyl, tert-butyl, 2-propyl or 1,1-dimethylhexyl. In certain embodiments each R$_2$ is methyl or tert-butyl.

X is —C(O)O—, —OC(O)—, —C(O)NR'—, —NR'C(O)—, —NR'—, —CH=N—, —C(O)—, —O—, —S—, —NR'— or —C(O)OC(O)—. In certain embodiments X is —NH—, —S— or —O—. In certain embodiments X is —O—. Optionally X is a bond.

M is an alkyl or

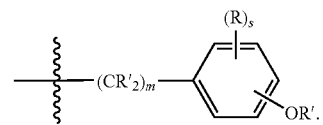

In certain embodiment M is alkyl. In certain other embodiments M is a C1-C20 linear or branched chain alkyl. In certain other embodiments M is a C5-C20 linear or branched chain alkyl. In certain other embodiments M is decane. Additionally M is —H;

each M' is independently —H, alkyl, or

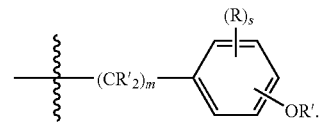

In certain embodiments, each M' is independently —H or alkyl;

each n is independently a positive integer from 1 to 6. In certain embodiments,
each n is independently integers from 1 to 4.
each m is independently 0 or a positive integer from 1 to 6. In certain embodiments, each m is independently integers from 0 to 4;
each q is independently an integer from 0 to 3. In certain embodiments q is 0;

k in each occurrence independently is a positive integer from 1 to 12;

l in each occurrence, independently is 0 or a positive integer from 1 to 12; and each s, q and u are independently integers from 0 to 4. In certain embodiments, each s and q are independently integers from 0 to 2. In other embodiments, s is 2. In certain embodiments, each s, and u are independently integers from 0 to 4; and r is an integer from 0 to 4. In other embodiments each s, q and r are independently integers from 0 to 2.

In a first embodiment for compounds of Structural formula III:

A is —C(O)O—, —OC(O)—, —C(O)NH—, —NHC(O)—, —NH—, —O— or —C(O)—;

R' is —H;

each R** is independently an optionally substituted alkyl or optionally substituted alkoxycarbonyl;

each $R_2$ is independently an optionally substituted alkyl;

X is —O—;

M is —H or an alkyl;

each n is independently integers from 1 to 4;

each m is independently integers from 0 to 4; and each s and q are independently integers from 0 to 2 and the remainder of the variables are as described above.

In a second embodiment for compounds of Structural formula III:

A is —C(O)NH— or —NHC(O)—;

each R** is independently an alkyl or an alkoxycarbonyl;

each $R_2$ is independently an alkyl; and s is 2 and the remainder of the variables are as described above in the first embodiment.

In a third embodiment for compounds of Structural formula III:

each R** is independently an alkyl group and the remainder of the variables are as described above in the second embodiment.

In a fourth embodiment for compounds of Structural formula III:

each R** is independently a tert-butyl group and the remainder of the variables are as described above in the third embodiment.

In a fifth embodiment for compounds of Structural formula III:

both R** are ortho to the —OH group and the remainder of the variables are as described above in the fourth embodiment.

In a first embodiment for compounds of Structural formula IV:

A is —C(O)O—, —OC(O)—, —C(O)NH—, —NHC(O)—, —NH—, —O— or —C(O)—;

R' is —H;

each R** is independently an optionally substituted alkyl or optionally substituted alkoxycarbonyl;

each $R_2$ is independently an optionally substituted alkyl.

each M' is independently —H or alkyl;

X is —O—;

each n is independently a positive integers from 1 to 4;

each m is independently 0 or a positive integer from 0 to 2; and each s, q and r are independently integers from 0 to 2 and the remainder of the variables are as described above.

In a second embodiment for compounds of Structural formula IV:

A is —C(O)NH— or —NHC(O)—;

each R** is independently an alkyl or an alkoxycarbonyl; and s is 2 and the remainder of the variables are as described above in the first embodiment.

In a third embodiment for compounds of Structural formula IV:

each R** is independently an alkyl group and the remainder of the variables are as described above in the second embodiment.

In a fourth embodiment for compounds of Structural formula IV:

each R** is independently a tert-butyl group and the remainder of the variables are as described above in the third embodiment.

In a fifth embodiment for compounds of Structural formula IV:

both R** are ortho to the —OH group and the remainder of the variables are as described above in the fourth embodiment.

In a third embodiment for compounds of Structural formula IV:

The term "alkyl" as used herein means a saturated straight-chain, branched or cyclic hydrocarbon. When straight-chained or branched, an alkyl group is typically C1-C20, more typically C1-C 10; when cyclic, an alkyl group is typically C3-C12, more typically C3-C7. Examples of alkyl groups include methyl, ethyl, n-propyl, iso-propyl, n-butyl, sec-butyl and tert-butyl and 1,1-dimethylhexyl.

An "aliphatic group" is non-aromatic, consists solely of carbon and hydrogen and may optionally contain one or more units of unsaturation, e.g., double and/or triple bonds. An aliphatic group may be straight-chained or branched and typically contains between 1 and 12 carbon atoms, more typically between 1 and 6 carbon atoms, and even more typically between 1 and 4 carbon atoms. An aliphatic group may be optionally substituted at any "substitutable carbon atom". A "substitutable carbon atom" in an aliphatic group is a carbon in the aliphatic group that is bonded to one or more hydrogen atoms. One or more hydrogen atoms can be optionally replaced with a suitable substituent group. A bivalent aliphatic group is a bivalent group represented by -aliphatic-, wherein aliphatic is an aliphatic group as defined above.

An "alkylene group" is represented by —[CH$_2$]$_z$—, wherein z is a positive integer, preferably from one to eight, more preferably from one to six, wherein optionally one or more hydrogen atoms are optionally replaced with suitable substituents. Suitable substituents for an alkylene group are as defined below for aliphatic groups. Preferred substituents include alkyl, hydroxyl, alkoxy, amine, alkylamine, dialkylamine, oxo, halo, hydroxyalkyl, alkoxyalkyl and aminoalkyl.

The term "alkoxy" as used herein is represented by —OR, wherein R is an alkyl group as defined above.

The term "carbonyl" as used herein is represented by —C(=O)R, wherein R is an alkyl group as defined above.

The term "alkoxycarbonyl" as used herein is represented by —C(=O)OR, wherein R is an alkyl group as defined above.

The term "aromatic group" includes carbocyclic aromatic rings and heteroaryl rings. The term "aromatic group" may be used interchangeably with the terms "aryl", "aryl ring" "aromatic ring", "aryl group" and "aromatic group".

Carbocyclic aromatic ring groups have only carbon ring atoms (typically six to fourteen) and include monocyclic aromatic rings such as phenyl and fused polycyclic aromatic ring systems in which a carbocyclic aromatic ring is fused to one or more aromatic rings (carbocyclic aromatic or heteroaromatic). Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (carbocyclic or heterocyclic), such as in an indanyl, phthalimidyl, naphthimidyl, phenanthridinyl, or tetrahydronaphthyl.

The term "heteroaryl", "heteroaromatic", "heteroaryl ring", "heteroaryl group" and "heteroaromatic group", used alone or as part of a larger moiety as in "heteroaralkyl" refers to heteroaromatic ring groups having five to fourteen members, including monocyclic heteroaromatic rings and polycyclic aromatic rings in which a monocyclic aromatic ring is fused to one or more other aromatic ring (carbocyclic or heterocyclic). Heteroaryl groups have one or more ring heteroatoms. Examples of heteroaryl groups include 2-furanyl, 3-furanyl, N-imidazolyl, 2-imidazolyl, 4-imidazolyl, 5-imidazolyl, 3-isoxazolyl, 4-isoxazolyl, 5-isoxazolyl, oxadiazolyl, oxadiazolyl, 2-oxazolyl, 4-oxazolyl, 5-oxazolyl, N-pyrazolyl, 3-pyrazolyl, 4-pyrazolyl, 5-pyrazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 4-pyridazinyl, 2-thiazolyl, 4-thiazolyl, 5-thiazolyl, triazolyl, tetrazolyl, 2-thienyl, 3-thienyl, carbazolyl, benzothienyl, benzofuranyl, indolyl, quinolinyl, benzothiazole, benzooxazole, benzimidazolyl, isoquinolinyl and isoindolyl. Also included within the scope of the term "heteroaryl", as it is used herein, is a group in which an aromatic ring is fused to one or more non-aromatic rings (carbocyclic or heterocyclic).

The term non-aromatic heterocyclic group used alone or as part of a larger moiety refers to non-aromatic heterocyclic ring groups having three to fourteen members, including monocyclic heterocyclic rings and polycyclic rings in which a monocyclic ring is fused to one or more other non-aromatic carbocyclic or heterocyclic ring or aromatic ring (carbocyclic or heterocyclic). Heterocyclic groups have one or more ring heteroatoms, and can be saturated or contain one or more units of unsaturation. Examples of heterocyclic groups include piperidinyl, piperizinyl, pyrrolidinyl, pyrazolidinyl, imidazolidinyl, tetrahydroquinolinyl, inodolinyl, isoindolinyl, tetrahydrofuranyl, oxazolidinyl, thiazolidinyl, dioxolanyl, dithiolanyl, tetrahydropyranyl, dihydropyranyl, azepanyl and azetidinyl The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heteroaryl or non-aromatic heterocyclic group. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl) or NR" (as in N-substituted pyrrolidinyl), wherein R" is a suitable substituent for the nitrogen atom in the ring of a non-aromatic nitrogen-containing heterocyclic group, as defined below. Preferably the nitrogen is unsubstituted.

As used herein the term non-aromatic carbocyclic ring as used alone or as part of a larger moiety refers to a non-aromatic carbon containing ring which can be saturated or contain one or more units of unsaturation, having three to fourteen atoms including monocyclic and polycyclic rings in which the carbocyclic ring can be fused to one or more non-aromatic carbocyclic or heterocyclic rings or one or more aromatic (carbocyclic or heterocyclic) rings An optionally substituted aryl group as defined herein may contain one or more substitutable ring atoms, such as carbon or nitrogen ring atoms. Examples of suitable substituents on a substitutable ring carbon atom of an aryl or aliphatic group include halogen (e.g., —Br, Cl, I and F), —OH, C1-C4 alkyl, C1-C4 haloalkyl, —NO$_2$, C1-C4 alkoxy, C1-C4 haloalkoxy, —CN, —NH$_2$, C1-C4 alkylamino, C1-C4 dialkylamino, —C(O)NH$_2$, —C(O)NH(C1-C4 alkyl), —C(O)(C1-C4 alkyl), —OC(O)(C1-C4 alkyl), —OC(O)(aryl), —OC(O)(substituted aryl), —OC(O)(aralkyl), —OC(O)(substituted aralkyl), —NHC(O)H, —NHC(O)(C1-C4 alkyl), —C(O)N(C1-C4 alkyl)$_2$, —NHC(O)OC1-C4 alkyl), —C(O)OH, —C(O)O—(C1-C4 alkyl), —NHC(O)NH$_2$, —NHC(O)NH (C1-C4 alkyl), —NHC(O)N(C1-C4 alkyl)$_2$, —NH—C (=NH)NH$_2$, —SO$_2$NH$_2$—SO$_2$NH(C1-C3alkyl), —SO$_2$N (C1-C3alkyl)$_2$, NHSO$_2$H, NHSO$_2$(C1-C4 alkyl) and aryl. Preferred substituents on aryl groups are as defined throughout the specification. In certain embodiments aryl groups are unsubstituted.

Examples of suitable substituents on a substitutable ring nitrogen atom of an aryl group include C1-C4 alkyl, NH$_2$, C1-C4 alkylamino, C1-C4 dialkylamino, —C(O)NH$_2$, —C(O)NH(C1-C4 alkyl), —C(O)(C1-C4 alkyl), —CO$_2$R, —C(O)C(O)R, —C(O)CH$_3$, —C(O)OH, —C(O)O—(C1-C4 alkyl), —SO$_2$NH$_2$—SO$_2$NH(C1-C3alkyl), —SO$_2$N(C1-C3alkyl)$_2$, NHSO$_2$H, NHSO$_2$(C1-C4 alkyl), —C(=S)NH$_2$, —C(=S)NH(C1-C4 alkyl), —C(=S)N(C1-C4 alkyl)$_2$, —C(=NH)—N(H)$_2$, —C(=NH)—NH(C1-C4 alkyl) and —C(=NH)—N(C1-C4 alkyl)$_2$, An optionally substituted alkyl group, alkylene, or aliphatic or non-aromatic carbocyclic or heterocyclic group as defined herein may contain one or more substituents. Examples of suitable substituents for an alkyl group include those listed above for a substitutable carbon of an aryl and aliphatic and the following: =O, =S, =NNHR, =NN(R)$_2$, =NNHC(O)R, =NNHCO$_2$ (alkyl), =NNHSO$_2$ (alkyl), =NR, spiro cycloalkyl group or fused cycloalkyl group. R** in each occurrence, independently is —H or C1-C6 alkyl. Preferred substituents on alkyl groups are as defined throughout the specification. In certain embodiments optionally substituted alkyl groups are unsubstituted.

A "spiro cycloalkyl" group is a cycloalkyl group which shares one ring carbon atom with a carbon atom in an alkylene group or alkyl group, wherein the carbon atom being shared in the alkyl group is not a terminal carbon atom.

As used herein, the terms "a bond" and "absent" to described possible values for the variables described herein can be used interchangeably.

In yet another embodiment, the present invention is a method of producing a compound described herein using methods know in the art of organic chemistry.

In certain embodiments this invention can allow synthesizing macromolecular antioxidants cost effectively. In these embodiments these methods also reports an improved, highly efficient and economical process for the synthesis of macromolecular antioxidants.

As used herein an "antioxidant moiety" is a molecule or a portion of a molecule which has itself antioxidant properties, for example a phenolic group. A molecule which has two phenolic groups has, for example, two antioxidant moieties, i.e, each phenolic group which is capable of acting as a proton donor is an antioxidant moiety.

The present invention relates to macromolecular compounds possessing antioxidant properties comprising more than one type of antioxidant moieties (for example, W1H and W2H), and methods of inhibiting oxidation in a substance comprising contacting the substance with the antioxidants described herein. This is achieved by coupling these unique structural units to di-, tri- and tetra-functional molecules providing a single macromolecule with multiple antioxidant moieties acting synergistically among themselves. The conceptual designs of these possible macromolecular antioxidants are shown here for the active parts of the molecule. The reaction activities of these antioxidant moieties are selected so that transfer equilibrium among the moieties is maintained so that regeneration of moieties is possible proving enhanced oxidation inhibition. This is illustrated below.

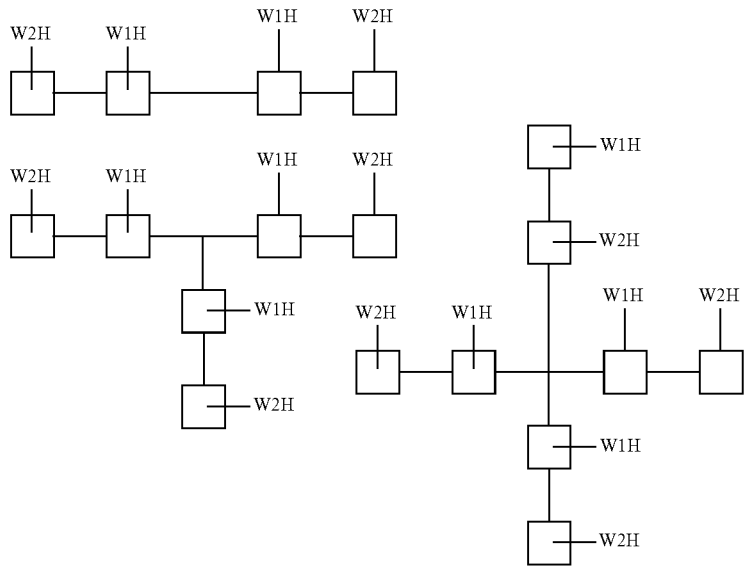

Consider a multifunctional antioxidant containing two different kinds of active moieties or (W1H and W2H), each of which is capable of acting as a hydrogen atom donor to a peroxy radical. With this multifunctional antioxidant there are two possible inhibition reactions (1a) and (1b):

    (1a)

    (1b)

The antioxidant is designed in such a way that the moiety W1H is much more reactive than the W2H i.e. $k_{1a} > k_{1b}$. In model oxidation studies conducted with antioxidants having similar warheads, the ratio $k_{1a}/k_{1b}$ is ~20.

The radicals derived from W1H and W2H present different levels of reactivity in propagation reaction (2). Once again, there are two possible propagation reactions (2a) and (2b):

    (2a)

    (2b)

In this multifunctional antioxidant, W1. is much more reactive than W2., i.e. $k_{2a} \gg k_{2b}$. In model studies conducted using antioxidants with similar warheads, only reaction (2a) could be observed.

The undesired propagation reaction (2a) is effectively prevented by a transfer equilibrium reaction (3), which regenerates the highly active antioxidant warhead W1H and gives the stable radical W2 as a by-product:

    (3)

The commercial antioxidants are normally sacrificial. It means that these molecules become inactive after they participated in the oxidation inhibiting event. On the contrary, the design of new antioxidants suggests (equation 3) that some of these antioxidant activities are regenerated through W1H while others are sacrificed (W2H) at the same time. The net result is that novel antioxidants provide extended protection.

In various embodiments, the macromolecular antioxidants of the present invention can be prepared as shown below:

In certain embodiments the present invention is a method of synthesizing a macromonomer represented by the following structural formula:

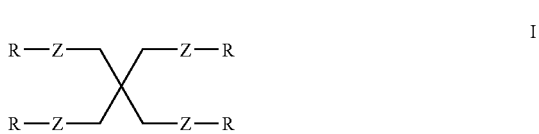                I wherein:

R is:

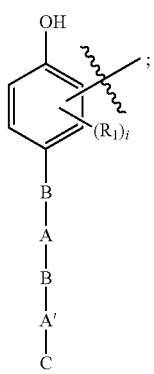

A in each occurrence, independently is —O—, —NH—, —S—, —C(O)—, —C(O)NH—, —NHC(O)—, —C(O)O—, —OC(O)—, —CH=N— or —N=CH—;

A' in each occurrence, independently is a bond, —O—, —NH—, —S—, —C(O)—, —C(O)NH—, —NHC(O)—, —C(O)O—, —OC(O)—, —CH=N— or —N=CH—;

B in each occurrence, independently is a bond or an optionally substituted alkylene group;

C in each occurrence independently is —H, an optionally substituted alkylene group or

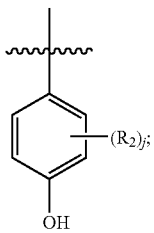

$R_1$ and $R_2$ in each occurrence, independently is an optionally substituted alkyl, optionally substituted aryl or optionally substituted aralkyl;

Z in each occurrence, independently is a bond, an optionally substituted alkylene group, —(CH$_2$)$_i$NHC(O)(CH$_2$)$_l$—, —(CH$_2$)$_l$C(O)NH(CH$_2$)$_l$—, —(CH$_2$)$_l$C(O)O(CH$_2$)$_l$—, —(CH$_2$)$_l$OC(O)(CH$_2$)$_l$—, —(CH$_2$)$_l$CH=N(CH$_2$)$_l$—, —(CH$_2$)$_l$N=CH(CH$_2$)$_l$—, —(CH$_2$)$_l$NH(CH$_2$)$_l$—, —(CH$_2$)$_l$S(CH$_2$)$_l$—, —(CH$_2$)$_l$—O(CH$_2$)$_l$— or —(CH$_2$)$_l$C(O)(CH$_2$)$_l$—;

i in each occurrence, independently is 0, 1, 2 or 3;
j in each occurrence, independently is 0, 1, 2, 3 or 4;
l in each occurrence, independently is 0 or a positive integer from 1 to 12;
comprising the step of combining $R^{++}$, wherein $R^{++}$ is:

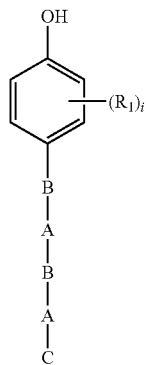

with X, wherein X is represented by the following structural formula:

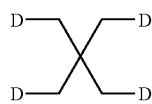

D in each occurrence, independently is halogen, haloalkyl, —(CH$_2$)$_l$—NHC(O)—F, —(CH$_2$)$_l$—C(O)NH—F, —(CH$_2$)$_l$—C(O)O—F, —(CH$_2$)$_l$—OC(O)—F, —(CH$_2$)$_l$—CH=N—F, —(CH$_2$)$_l$—N=CH—F, —(CH$_2$)$_l$—NH—F, —(CH$_2$)$_l$—S—F, —(CH$_2$)$_l$O—F or —(CH$_2$)$_l$—C(O)—F; and F in each occurrence, independently is —H, halogen, haloalkyl or an aliphatic group.

In certain embodiments: D in each occurrence, independently is —(CH$_2$)$_l$—C(O)O—F, —(CH$_2$)$_l$—OC(O)—F, —(CH$_2$)$_l$O—F or —(CH$_2$)$_l$—C(O)—F;

F in each occurrence, independently is —H, halogen, or a C1-C3 alkenyl group; and l in each occurrence, independently is 0 or a positive integer from 1 to 6.

In certain other embodiments, D in each occurrence, independently is —(CH$_2$)$_l$O—F, —(CH$_2$)$_l$—C(O)O—F or —(CH$_2$)$_l$—OC(O)—F;

F in each occurrence, independently is —H or a C1-C3 alkenyl group; and l in each occurrence, independently is 0 or a positive integer from 1 to 3.

In certain other embodiments X is:

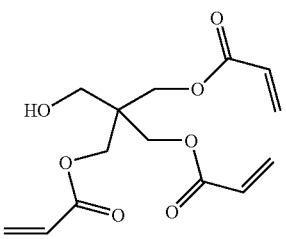

In certain other embodiments, $R^{++}$ is:

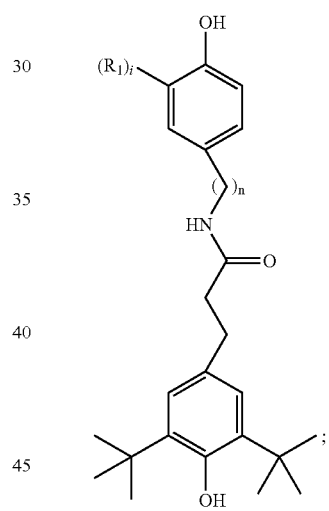

wherein:
n is an integer from 0 to 4;
i is 0 or 1; and
$R_1$ is a C1-C6 alkyl.

In certain other embodiments, the macromonomer is represented by the following structural formula:

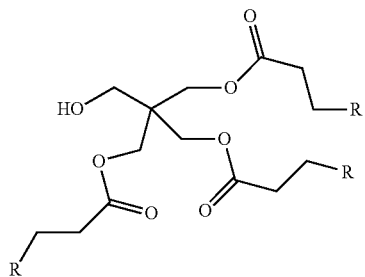

-continued

R = [structure: HO-phenyl(R1)i-(CH2)n-NH-C(O)-CH2CH2-phenyl(di-tert-butyl)-OH]

In certain embodiments the present invention is a method of synthesizing a macromonomer represented by the following structural formula:

$$\begin{array}{c} R-Z \\ R-Z \end{array} \diagdown \diagup \begin{array}{c} Z-R \\ Z-R \end{array} \qquad I$$

wherein:
R is:

[structure: OH-phenyl(R1)i-B-A-B-A'-C]

A in each occurrence, independently is —O—, —NH—, —S—, —C(O)—, —C(O)NH—, —NHC(O)—, —C(O)O—, —OC(O)—, —CH=N— or —N=CH—;

A' in each occurrence, independently is a bond, —O—, —NH—, —S—, —C(O)—, —C(O)NH—, —NHC(O)—, —C(O)O—, —OC(O)—, —CH=N— or —N=CH—;

B in each occurrence, independently is a bond or an optionally substituted alkylene group;

C in each occurrence independently is —H, an optionally substituted alkylene group or

[structure: phenyl(R2)j with OH]

$R_1$ and $R_2$ in each occurrence, independently is an optionally substituted alkyl, optionally substituted aryl or optionally substituted aralkyl;

Z in each occurrence, independently is a bond, an optionally substituted alkylene group, —(CH$_2$)$_i$NHC(O)(CH$_2$)$_l$—, —(CH$_2$)$_l$C(O)NH(CH$_2$)$_i$—, —(CH$_2$)$_l$C(O)O(CH$_2$)$_i$—, —(CH$_2$)$_l$OC(O)(CH$_2$)$_i$—, —(CH$_2$)$_l$CH=N(CH$_2$)$_i$—, —(CH$_2$)$_l$N=CH(CH$_2$)$_i$—, —(CH$_2$)$_l$NH(CH$_2$)$_i$—, —(CH$_2$)$_l$S(CH$_2$)$_i$—, —(CH$_2$)$_l$O(CH$_2$)$_i$— or —(CH$_2$)$_l$C(O)(CH$_2$)$_i$—;

i in each occurrence, independently is 0, 1, 2 or 3;

j in each occurrence, independently is 0, 1, 2, 3 or 4;

l in each occurrence, independently is 0 or a positive integer from 1 to 12; and comprising the step of combining R$^{+++}$, wherein R$^{+++}$ is:

[structure: OH-phenyl-D, (R1)i, -B-A-B-A-C]

with X', wherein X' is represented by the following structural formula:

[structure: Q-C(-Q)(-Q)-Q central carbon with four Q groups]

Q is —OH, NH$_2$ or SH;

D is halogen, haloalkyl, —(CH$_2$)$_l$—NHC(O)—F, —(CH$_2$)$_l$—C(O)NH—F, —(CH$_2$)$_l$—C(O)O—F, —(CH$_2$)$_l$—OC(O)—F, —(CH$_2$)$_l$—CH=N—F, —(CH$_2$)$_l$—N=CH—F, —(CH$_2$)$_l$—NH—F, —(CH$_2$)$_l$—S—F, —(CH$_2$)$_l$—O—F or —(CH$_2$)$_l$—C(O)—F; and F in each occurrence, independently is —H, halogen, haloalkyl or an aliphatic group.

In certain embodiments, D is —(CH$_2$)$_l$—C(O)O—F, —(CH$_2$)$_l$—OC(O)—F, —(CH$_2$)$_l$O—F or —(CH$_2$)$_l$—C(O)—F;

F is —H or halogen; and l in each occurrence, independently is 0 or a positive integer from 1 to 6.

In certain other embodiments, D is —(CH$_2$)$_l$—C(O)O—F or —(CH$_2$)$_l$—OC(O)—F; and F is —H; and l in each occurrence, independently is 0 or a positive integer from 1 to 3.

In certain other embodiments, X' is:

[structure: pentaerythritol: C(CH2OH)4, drawn as HO-CH2, HO-CH2, central C, -CH2-OH, -CH2-OH]

In certain other embodiments, R+++ is:

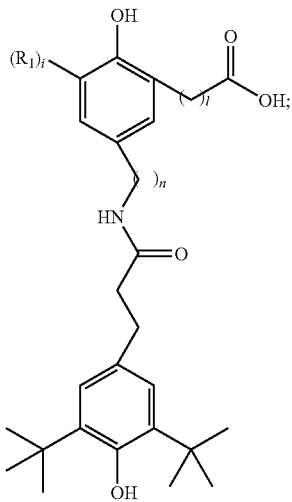

wherein:

n is an integer from 0 to 4;

l is i an integer from 0 to 2;

i is 0 or 1; and

R₁ is C1-C6 alkyl.

In certain other embodiments, the macromonomer is represented by the following structural formula:

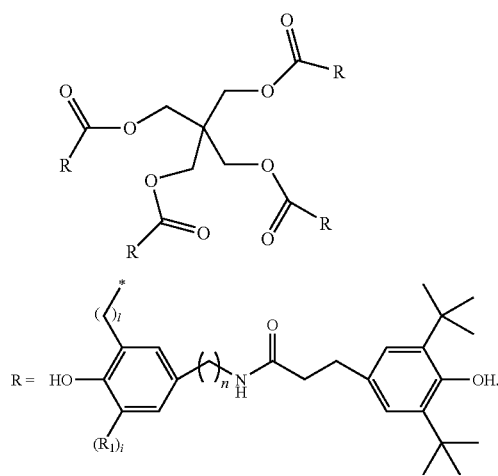

In certain embodiments the present invention is a method of synthesizing a macromonomer represented by the following structural formula:

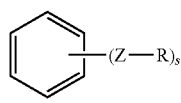
II wherein:

R is:

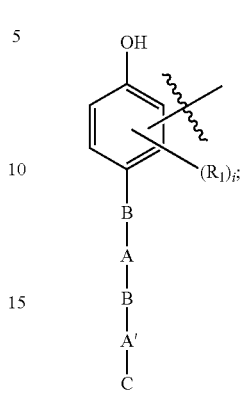

A in each occurrence, independently is —O—, —NH—, —S—, —C(O)—, —C(O)NH—, —NHC(O)—, —C(O)O—, —OC(O)—, —CH=N— or —N=CH—;

A' in each occurrence, independently is a bond, —O—, —NH—, —S—, —C(O)—, —C(O)NH—, —NHC(O)—, —C(O)O—, —OC(O)—, —CH=N— or —N=CH—;

B in each occurrence, independently is a bond or an optionally substituted alkylene group;

C in each occurrence independently is —H, an optionally substituted alkylene group or

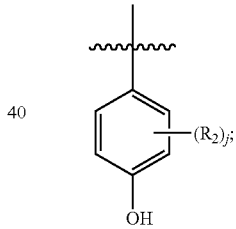

R₁ and R₂ in each occurrence, independently is an optionally substituted alkyl, optionally substituted aryl or optionally substituted aralkyl;

Z in each occurrence, independently is a bond, an optionally substituted alkylene group, —CH₂)ᵢNHC(O)(CH₂)ᵢ—, —(CH₂)ᵢC(O)NH(CH₂)ᵢ—, —(CH₂)ᵢC(O)O(CH₂)ᵢ—, —(CH₂)ᵢOC(O)(CH₂)ᵢ—, —(CH₂)ᵢCH=N(CH₂)ᵢ—, —(CH₂)ᵢN=CH(CH₂)ᵢ—, —(CH₂)ᵢNH(CH₂)ᵢ—, —(CH₂)ᵢS(CH₂)ᵢ—, —(CH₂)ᵢO(CH₂)ᵢ— or —(CH₂)ᵢC(O)(CH₂)ᵢ—;

i in each occurrence, independently is 0, 1, 2 or 3;

j in each occurrence, independently is 0, 1, 2, 3 or 4;

l in each occurrence, independently is 0 or a positive integer from 1 to 12;

s is a positive integer from 1 to 6;

comprising the step of combining R''', wherein R''' is:

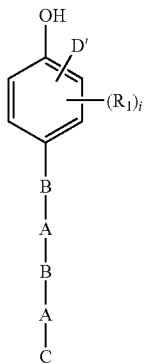

with X'', wherein X'' is represented by the following structural formula:

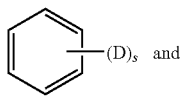

D is halogen, haloalkyl, —(CH$_2$)$_l$—NHC(O)—F, —(CH$_2$)$_l$—C(O)NH—F, —(CH$_2$)$_l$—C(O)O—F, —(CH$_2$)$_l$—OC(O)—F, —(CH$_2$)$_l$—CH=N—F, —(CH$_2$)$_l$—N=CH—F, —(CH$_2$)$_l$—NH—F, —(CH$_2$)$_l$—S—F, —(CH$_2$)$_l$O—F or —(CH$_2$)$_l$—C(O)—F; and D' is —(CH$_2$)$_l$—C(O)O—F, —(CH$_2$)$_l$—OC(O)—F or —(CH$_2$)$_l$O—F'; and F in each occurrence, independently is —H, halogen, haloalkyl or an aliphatic group; and F' in each occurrence, independently is —H, halogen, haloalkyl or an aliphatic group.

In certain embodiments,

D is —(CH$_2$)$_l$—C(O)O—F, —(CH$_2$)$_l$—OC(O)—F, —(CH$_2$)$_l$O—F or —(CH$_2$)$_l$—C(O)—F;

F in each occurrence, independently is —H, halogen, or a C1-C3 alkenyl group; and l in each occurrence, independently is 0 or a positive integer from 1 to 6;

In certain other embodiments,

D' is —(CH$_2$)$_l$O—F;

D is —(CH$_2$)$_l$—C(O)—F;

F is halogen;

F' is —H; and l in each occurrence, independently is 0 or a positive integer from 1 to 3.

In certain other embodiments, X'' is:

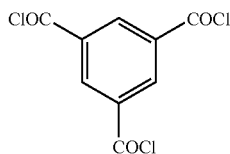

In certain other embodiments, R$^{+++}$ is:

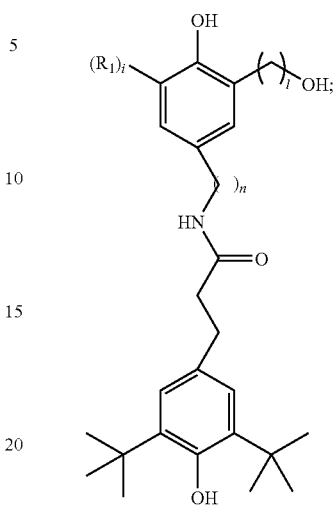

wherein n is an integer from 0 to 2;

l is i an integer from 0 to 2;

i is 0 or 1; and

R$_1$ is —H or optionally substituted alkyl.

In certain other embodiments, the macromonomer is represented by the following structural formula:

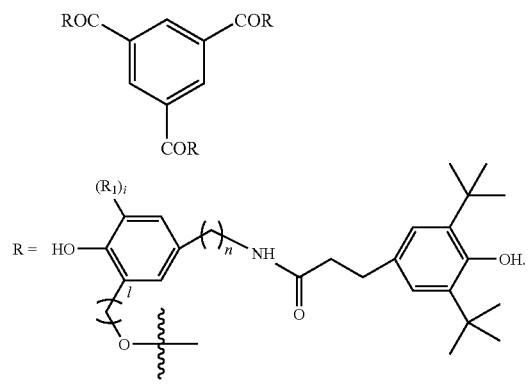

In certain embodiments the present invention is a method of synthesizing a macromonomer represented by the following structural formula:

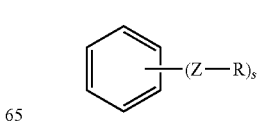

II wherein:

R is:

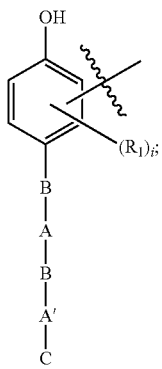

in each occurrence, independently is —O—, —NH—, —S—, —C(O)—, —C(O)NH—, —NHC(O)—, —C(O)O—, —OC(O)—, —CH=N— or —N=CH—;

A' in each occurrence, independently is a bond, —O—, —NH—, —S—, —C(O)—, —C(O)NH—, —NHC(O)—, —C(O)O—, —OC(O)—, —CH=N— or —N=CH—;

B in each occurrence, independently is a bond or an optionally substituted alkylene group;

C in each occurrence independently is —H, an optionally substituted alkylene group or

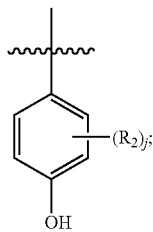

$R_1$ and $R_2$ in each occurrence, independently is an optionally substituted alkyl, optionally substituted aryl or optionally substituted aralkyl;

Z in each occurrence, independently is a bond, an optionally substituted alkylene group, —$(CH_2)_l$NHC(O)$(CH_2)_l$—, —$(CH_2)_l$C(O)NH$(CH_2)_l$—, —$(CH_2)_l$C(O)O$(CH_2)_l$—, —$(CH_2)_l$OC(O)$(CH_2)_l$—, —$(CH_2)_l$CH=N$(CH_2)_l$—, —$(CH_2)_l$N=CH$(CH_2)_l$—, —$(CH_2)_l$NH$(CH_2)_l$—, —$(CH_2)_l$S$(CH_2)_l$—, —$(CH_2)_l$O$(CH_2)_l$— or —$(CH_2)_l$C(O)$(CH_2)_l$—;

i in each occurrence, independently is 0, 1, 2 or 3;

j in each occurrence, independently is 0, 1, 2, 3 or 4;

l in each occurrence, independently is 0 or a positive integer from 1 to 12;

s is a positive integer from 1 to 6;

comprising the step of combining R*, wherein R* is:

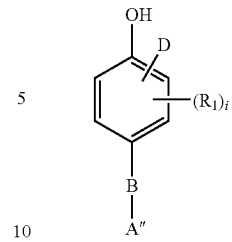

with X''', wherein X''' is represented by the following structural formula:

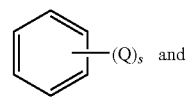

A" is $NO_2$, $NH_2$ or OH;

Q is —OH;

D is halogen, haloalkyl, —$(CH_2)_l$—NHC(O)—F, —$(CH_2)_l$—C(O)NH—F, —$(CH_2)_l$—C(O)O—F, —$(CH_2)_l$—OC(O)—F, —$(CH_2)_l$—CH=N—F, —$(CH_2)_l$—N=CH—F, —$(CH_2)_l$—NH—F, —$(CH_2)_l$—S—F, —$(CH_2)_l$O—F or —$(CH_2)_l$—C(O)—F; and F in each occurrence, independently is —H, halogen, haloalkyl or an aliphatic group;

to produce Y, wherein Y is represented by the following structural formula:

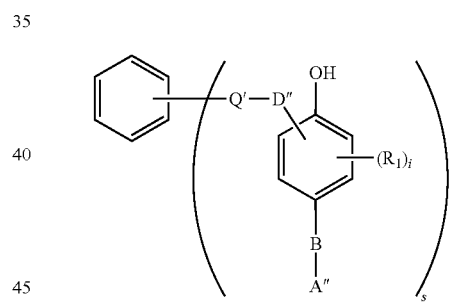

wherein:

Q' is —O—;

D" is a bond, alkylene, —$(CH_2)_l$—NHC(O)—F", —$(CH_2)_l$—C(O)NH—F", —$(CH_2)_l$—C(O)O—F", —$(CH_2)_l$—OC(O)—F", —$(CH_2)_l$—CH=N—F", —$(CH_2)_l$—N=CH—F", —$(CH_2)_l$—NH—F", —$(CH_2)_l$—S—F, —$(CH_2)_l$O—F" or —$(CH_2)_l$—C(O)—F"; and F" in each occurrence is absent or bivalent aliphatic group.

In certain embodiments, D is halogen or haloalkyl.

In certain other embodiments, X''' is:

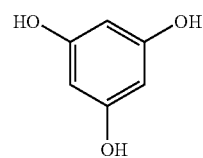

In certain other embodiments, R* is:

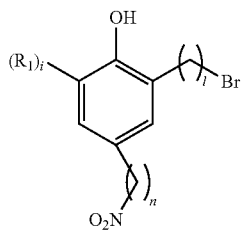

In certain other embodiments, the method further comprises the step of combining Y with U, wherein U is represented by the following structural formula:

wherein:
G is —COOH or COOalkyl
to produce the macromonomer.
In certain embodiments, U is:

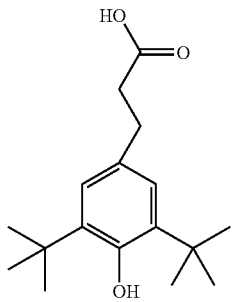

In certain other embodiments, the macromonomer is represented by the following structural formula:

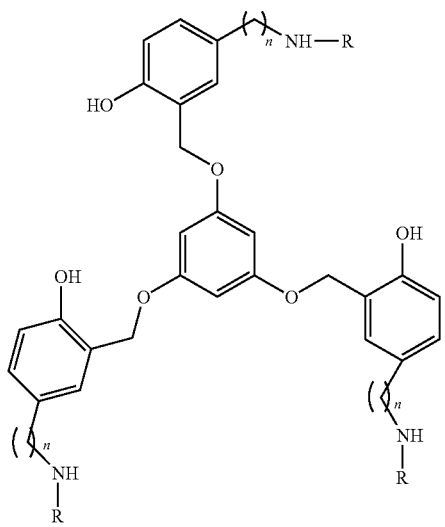

-continued

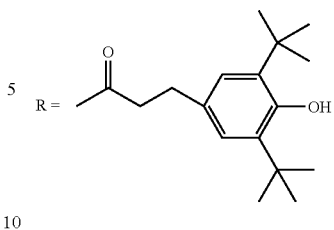

Scheme-1:

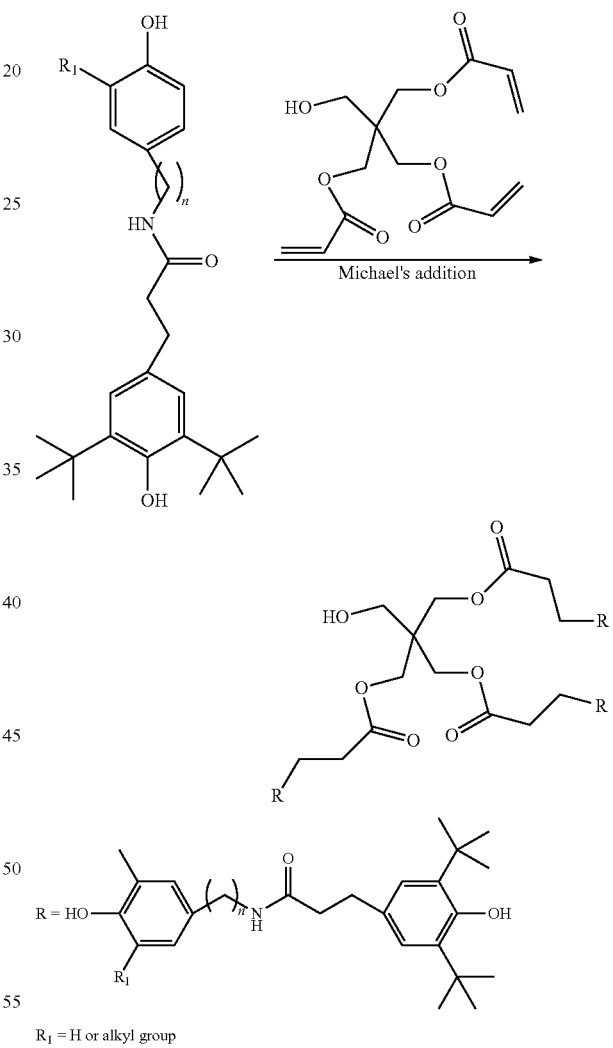

$R_1$ = H or alkyl group

The compounds in Scheme I in general are synthesized by dissolving a phenol in THF in the presence of a base (such as potassium-t-butoxide) and reacting the resultant carbanions with an acrylate under Michael's addition reaction conditions. N-methyl pyrollodine, dichlorobenzene and dimethoxy benzene are the other solvents that can used in the reaction. The reaction can also be done using sodium or potassium methoxide, lithium diisopropylamide (LDA)

Scheme-2:

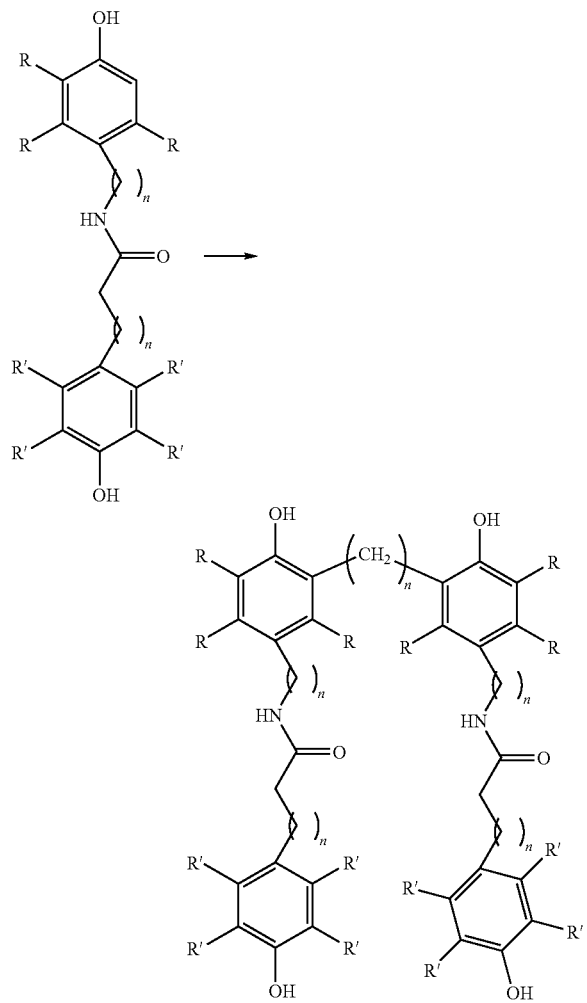

The compound shown in Scheme II in general are synthesized by reacting a phenol with formaldehyde in a suitable solvent in the presence of acidic or basic catalyst at a temperature 40° C.-130° C. The solvents which are suitable in this reaction includes methanol, ethanol, toluene.

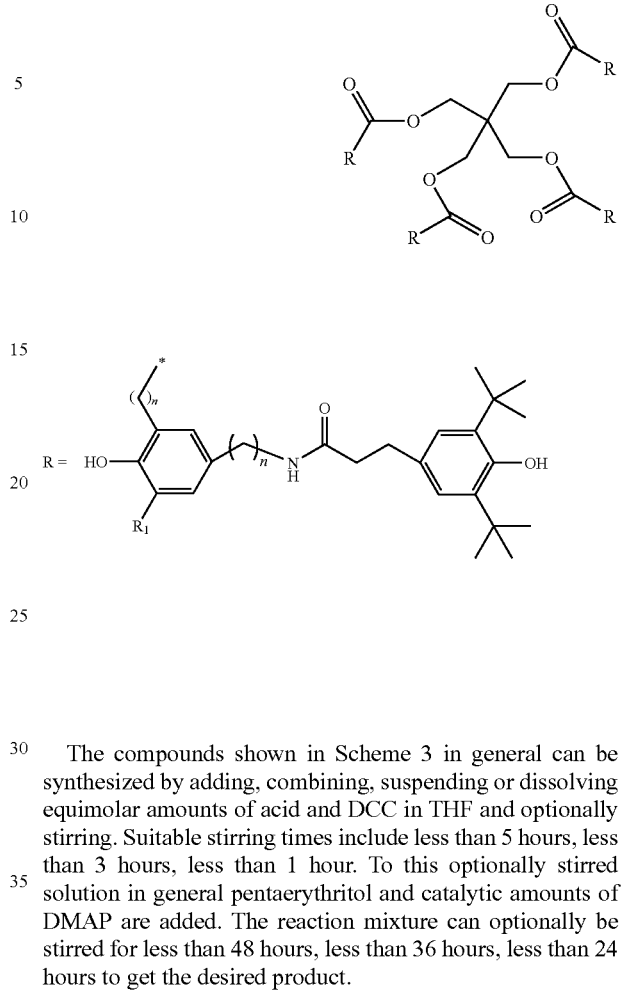

The compounds shown in Scheme 3 in general can be synthesized by adding, combining, suspending or dissolving equimolar amounts of acid and DCC in THF and optionally stirring. Suitable stirring times include less than 5 hours, less than 3 hours, less than 1 hour. To this optionally stirred solution in general pentaerythritol and catalytic amounts of DMAP are added. The reaction mixture can optionally be stirred for less than 48 hours, less than 36 hours, less than 24 hours to get the desired product.

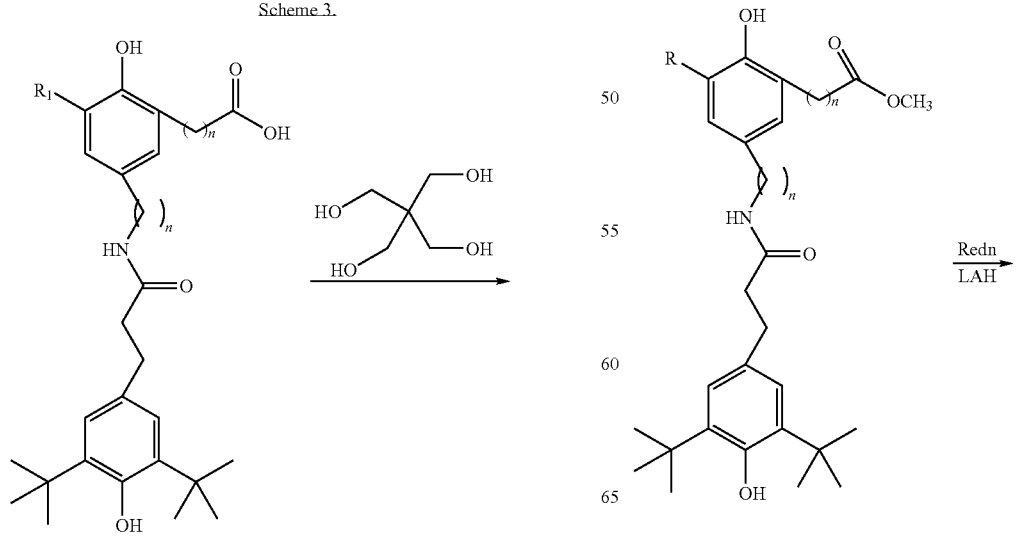

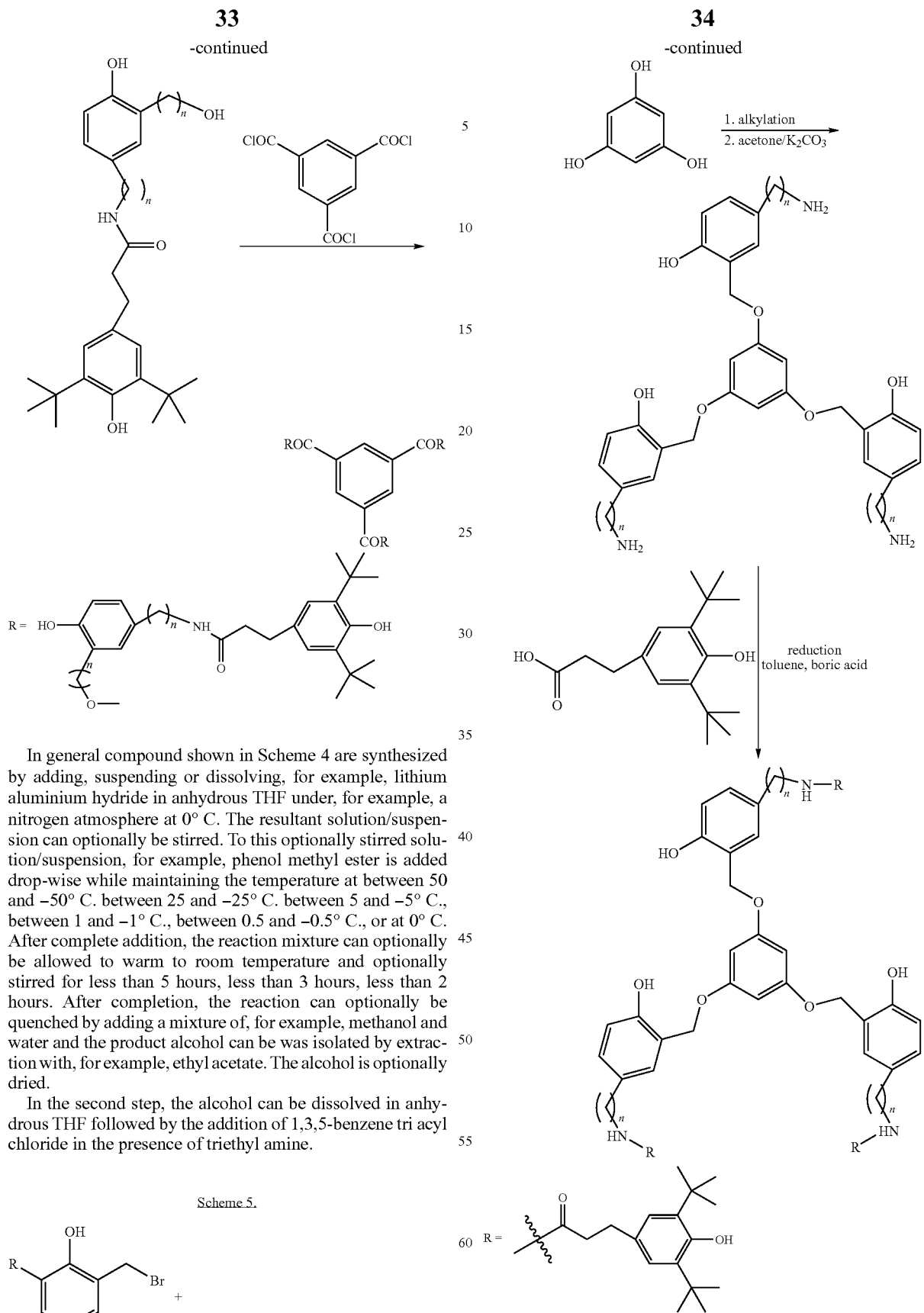

In general compound shown in Scheme 4 are synthesized by adding, suspending or dissolving, for example, lithium aluminium hydride in anhydrous THF under, for example, a nitrogen atmosphere at 0° C. The resultant solution/suspension can optionally be stirred. To this optionally stirred solution/suspension, for example, phenol methyl ester is added drop-wise while maintaining the temperature at between 50 and −50° C. between 25 and −25° C. between 5 and −5° C., between 1 and −1° C., between 0.5 and −0.5° C., or at 0° C. After complete addition, the reaction mixture can optionally be allowed to warm to room temperature and optionally stirred for less than 5 hours, less than 3 hours, less than 2 hours. After completion, the reaction can optionally be quenched by adding a mixture of, for example, methanol and water and the product alcohol can be was isolated by extraction with, for example, ethyl acetate. The alcohol is optionally dried.

In the second step, the alcohol can be dissolved in anhydrous THF followed by the addition of 1,3,5-benzene tri acyl chloride in the presence of triethyl amine.

The compound shown in scheme 5 can be prepared in three steps starting with, for example, trihydroxy benzene (phloroglucinol). Phloroglucinol can be alkylated with, for example, 5-nitro, 2-phenol benzyl bromide by dissolving in acetone in the presence of potassium carbonate. In the next step the alkylated nitrophenol can be reduced to alkylated phenol amine using tin and hydrochloric acid. The Alkylated phenol amine can be condensed with, for example, 3-(2,6-di-tert-butylphenol) propanoic acid to obtain the desired compound.

Structure 1.

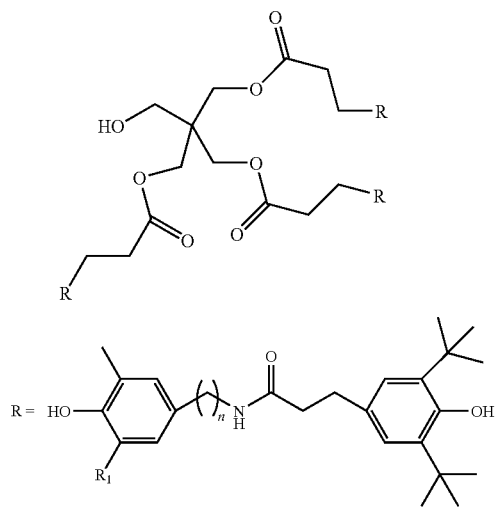

R$_1$=H or alkyl group

Structure 2.

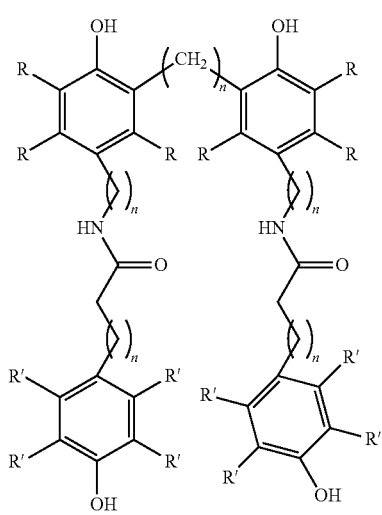

Structure 3.

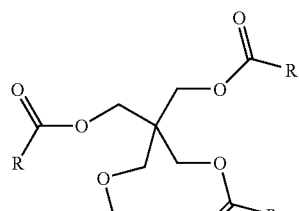

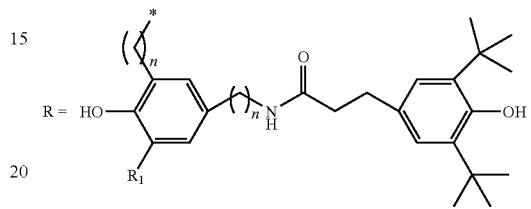

Structure 4.

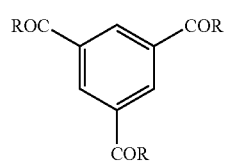

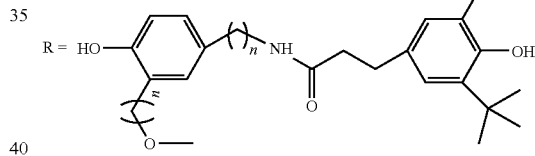

Structure 5.

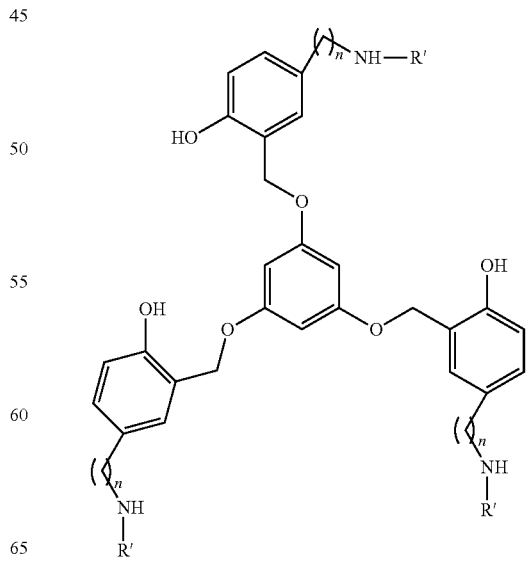

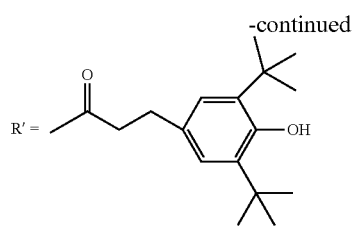

In various embodiments, the compounds of the present invention can be prepared as shown in the following Scheme:

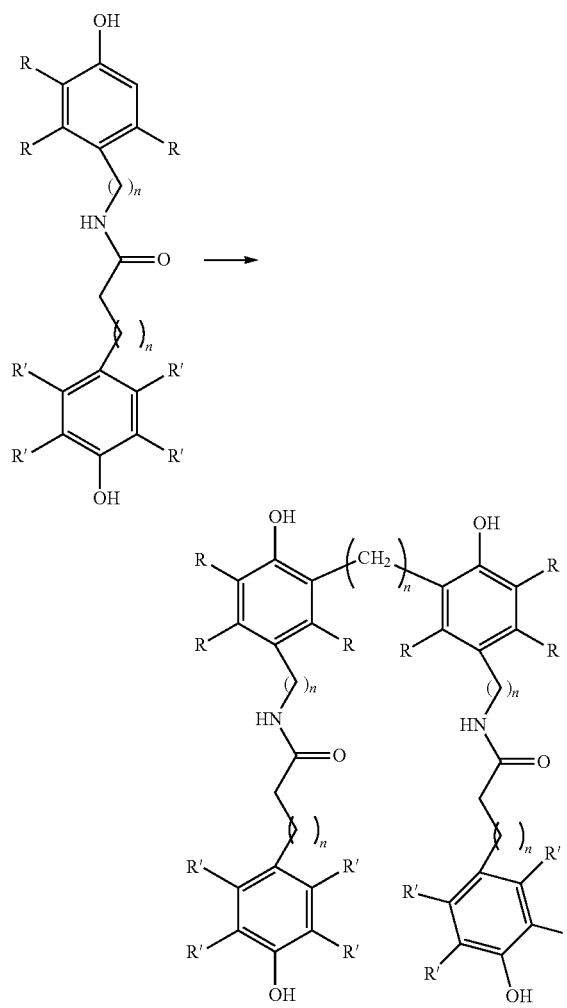

In certain embodiments the present invention is a method of making the compounds of the present invention comprising the steps of dissolving or suspending the starting material in a suitable solvent, such as, methanol or ethanol; adding a suitable reagent, such as, an aldehyde, for example, paraformaldehyde under suitable acidic conditions, such as, for example in the presence of hydrochloric acid. The mixture of the starting material, solvent acid and reagent can then be refluxed at between 0 and 100° C., between 10 and 90° C., between 20 and 80° C., between 40 and 70° C. or between 60 and 70° C. The progress of the reaction can be monitored by thin-layer chromatography. After completion of the reaction the solvent can be removed by distillation under vacuum. The remaining solid can then be washed with water and dried to obtain the polymer.

In various embodiments, the compounds of the present invention can be prepared as shown in the following Scheme:

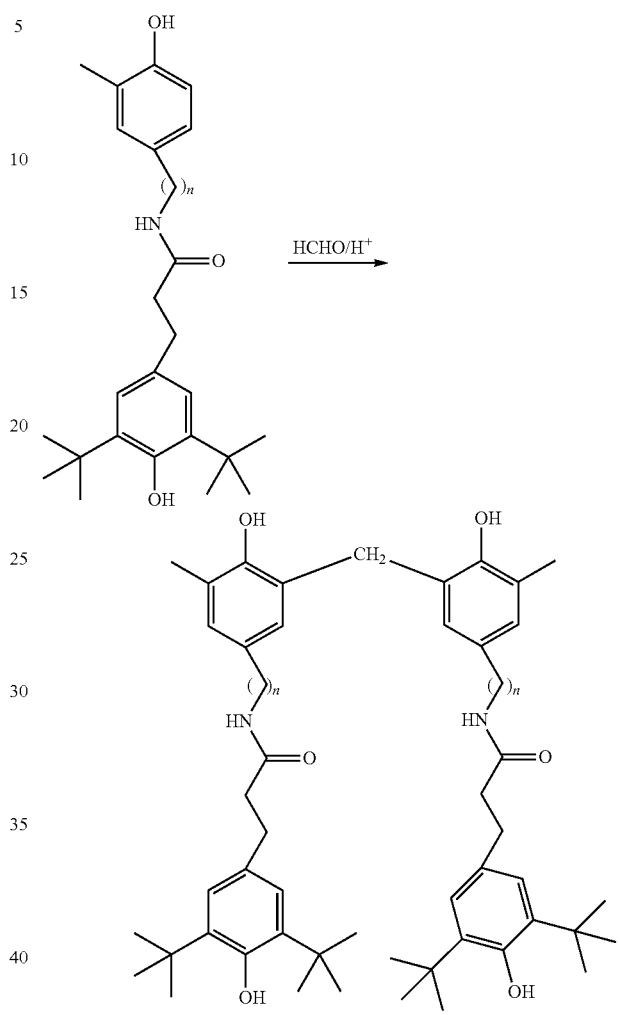

In various embodiments, the compounds of the present invention can be prepared as shown in the following scheme:

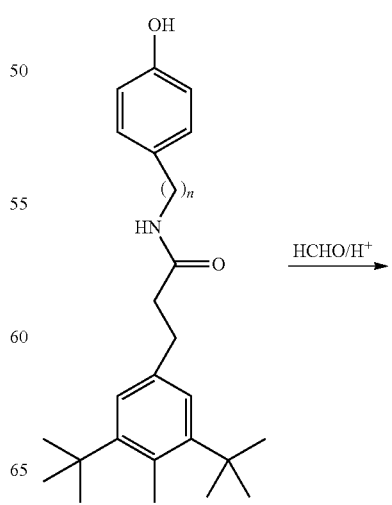

-continued

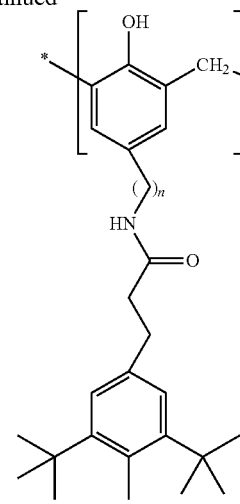

In certain embodiments the present invention is a method of making a compound represented by the following Structural Formula:

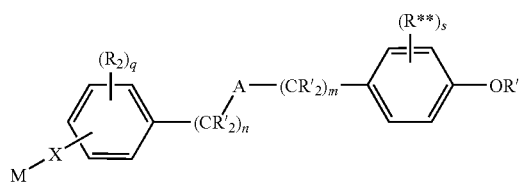

wherein:
A is —C(O)NR'—, —NR'C(O)—, —NR'—, —CR'=N—, —C(O)—, —C(O)O—, —OC(O)—, —O—, —S—, —C(O)OC(O)— or a bond;
each R' is independently —H or optionally substituted alkyl;
each R** is independently an optionally substituted alkyl, optionally substituted aryl, optionally substituted alkoxycarbonyl, optionally substituted ester, —OH, —NH$_2$, —SH, or

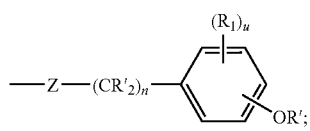

each R$_1$ and R$_2$ is independently an optionally substituted alkyl, optionally substituted aryl, optionally substituted alkoxycarbonyl, optionally substituted ester, —OH, —NH$_2$ or —SH;
X is —C(O)O—, —OC(O)—, —C(O)NR'—, —NR'C(O)—, —NR'—, —CH=N—, —C(O)—, —O—, —S—, —NR'— or —C(O)OC(O)—;
M is —H, an alkyl or

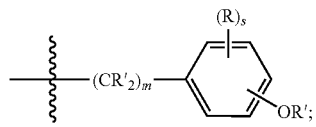

each n is independently a positive integer from 1 to 6;
each m is independently 0 or a positive integer from 1 to 6; and each s, q and u are independently integers from 0 to 4;
comprising the steps of combining G, wherein G is represented by the following structural formula:

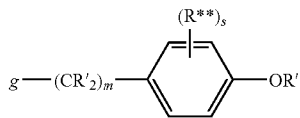

wherein g is a phenolic acid with H, wherein H is represented by the following structural formula:

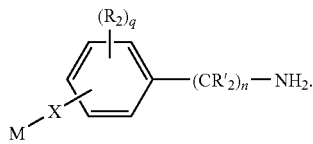

In another embodiment the present invention is a method of making a compound represented by the following Structural Formula:

R—Z—(CH$_2$)$_k$—Z—R wherein R is:

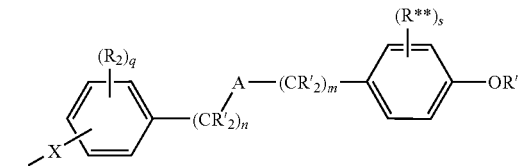

A is —C(O)NR'—, —NR'C(O)—, —NR'—, —CR'=N—, —C(O)—, —C(O)O—, —OC(O)—, —O—, —S—, —C(O)OC(O)— or a bond;
Z in each occurrence, independently is a bond, an optionally substituted alkylene group, —(CH$_2$), NHC(O)(CH$_2$)$_f$—, —(CH$_2$)$_f$C(O)NH(CH$_2$)$_f$—, —(CH$_2$)$_f$C(O)O(CH$_2$)$_f$—, —(CH$_2$)$_f$OC(O)(CH$_2$)$_f$—, —(CH$_2$)$_f$CH=N(CH$_2$)$_f$—, —(CH$_2$)$_f$N=CH(CH$_2$)$_f$—, —(CH$_2$)$_f$NH(CH$_2$)$_f$—, —(CH$_2$)$_f$S(CH$_2$)$_f$—, —(CH$_2$)$_f$—O(CH$_2$)$_f$— or —(CH$_2$)$_f$C(O)(CH$_2$)$_f$—;
each R' is independently —H or optionally substituted alkyl;
each R** is independently an optionally substituted alkyl, optionally substituted aryl, optionally substituted alkoxycarbonyl, optionally substituted ester, —OH, —NH$_2$, —SH, or

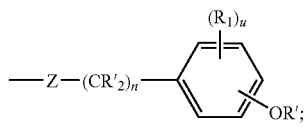

each R$_1$ and R$_2$ is independently an optionally substituted alkyl, optionally substituted aryl, optionally substituted alkoxycarbonyl, optionally substituted ester, —OH, —NH$_2$ or —SH;
X is —C(O)O—, —OC(O)—, —C(O)NR'—, —NR'C(O)—, —NR'—, —CR'=N—, —C(O)—, —O—, —S—, —NR'— or —C(O)OC(O)—;
each M' is independently —H, alkyl, or

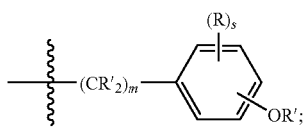

each n is independently a positive integer from 1 to 6;
each m is independently 0 or a positive integer from 1 to 6;
l in each occurrence, independently is 0 or a positive integer from 1 to 12; and
k in each occurrence independently is a positive integer from 1 to 12;
each q is independently an integer from 0 to 3;
each s, and u are independently integers from 0 to 4; and
r is an integer from 0 to 4;
comprising the steps of polymerizing a compound represented by the following structural formula:

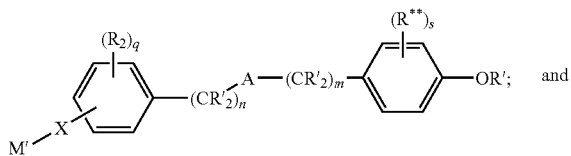

isolating the polymer.

In certain embodiments these macromolecular antioxidants can have significantly higher antioxidant activities along with improved thermal stability and performance in a wide range of materials including but not limited to plastics, elastomers, lubricants, petroleum based products (lubricants, gasoline, aviation fuels, and engine oils), cooking oil, cosmetics, processed food products, compared to commercially available antioxidants. In certain embodiments the present invention also discloses the superior performance of macromolecules of the formula I in materials including but not limited to polyolefins.

The compounds of the present invention can be used as antioxidants to inhibit oxidation of an oxidizable material. Such as, for example to increase the shelf life of an oxidizable material.

The antioxidant compounds of the present invention can be employed to inhibit the oxidation of an oxidizable material, for example by contacting the material with an antioxidant compound of the present invention.

For purposes of the present invention, a method of "inhibiting oxidation" is a method that inhibits the propagation of a free radical-mediated process. Free radicals can be generated by heat, light, ionizing radiation, metal ions and some proteins and enzymes. Inhibiting oxidation also includes inhibiting reactions caused by the presence of oxygen, ozone or another compound capable of generating these gases or reactive equivalents of these gases.

As used herein the term "oxidizable material" is any material which is subject to oxidation by free-radicals or oxidative reaction caused by the presence of oxygen, ozone or another compound capable of generating these gases or reactive equivalents thereof.

In certain embodiments, the oxidizable material is an organic polymer or plastic. In certain embodiments, the oxidizable material is an elastomer. In certain embodiments, the oxidizable material is a lubricant. In certain embodiments, the oxidizable material is a petroleum based product. In certain embodiments, the oxidizable material is an edible oil or cooking oil. In certain embodiments, the oxidizable material is a cosmetic. In certain embodiments, the oxidizable material is a processed food product.

In particular the oxidizable material is a lubricant or a mixture of lubricants.

The shelf life of many materials and substances contained within the materials, such as packaging materials, are enhanced by the presence of the antioxidants of the present invention. The addition of an antioxidant of the present invention to a packaging material is believed to provide additional protection to the product contained inside the package. In addition, the properties of many packaging materials themselves, particularly polymers, are enhanced by the presence of an antioxidant regardless of the application (i.e., not limited to use in packaging). Common examples of packaging materials include paper, cardboard and various plastics and polymers. A packaging material can be coated with an antioxidant (e.g., by spraying the antioxidant or by applying as a thin film coating), blended with or mixed with an antioxidant, or otherwise have an antioxidant present within it. In one example, a thermoplastic such as polyethylene, polypropylene or polystyrene can be melted in the presence of an antioxidant in order to minimize its degradation during the polymer processing.

The lifetime of lubricants, lubricant oils, mixtures thereof and compositions comprising lubricants and lubricant oils in general can be improved by contacting the lubricant, lubricant oil, mixtures thereof or composition comprising the lubricant or lubricant oil or mixtures thereof with compounds of the present invention, as described herein.

In certain embodiments of the present invention, polyolefins and mixtures of polyolefins can be stabilized by contacting the polyolefin or mixture of polyolefins with a compound of the present invention. These polyolefins and mixtures of polyolefins, include, but are not limited to substituted polyolefins, polyacrylates, polymethacrylates and copolymers of polyolefins. The following are examples of some types of polyolefins which can be stabilized by the methods of the present invention:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), very low density polyethylene (VLDPE) and ultra low density polyethylene (ULDPE).

Polyolefins, i.e. the polymers of monoolefins exemplified in the preceding paragraph, for example polyethylene and polypropylene, can be prepared by different, and especially by the following, methods:

i) radical polymerization (normally under high pressure and at elevated temperature).

ii) catalytic polymerization using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either p- or s-coordinated. These metal complexes may be in the free form or fixed on substrates, typically on activated magnesium chloride, titanium(III) chloride, alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1., for example, mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

4. Blends of polymers mentioned under 1. with impact modifiers such as ethylene-propylene-diene monomer copolymers (EPDM), copolymers of ethylene with higher alpha-olefins (such as ethylene-octene copolymers), polybutadiene, polyisoprene, styrene-butadiene copolymers, hydrogenated styrene-butadiene copolymers, styrene-isoprene copolymers, hydrogenated styrene-isoprene copolymers. These blends are commonly referred to in the industry as TPO's (thermoplastic polyolefins).

In certain particular embodiments polyolefins of the present invention are for example polypropylene homo- and copolymers and polyethylene homo- and copolymers. For instance, polypropylene, high density polyethylene (HDPE), linear low density polyethylene (LLDPE) and polypropylene random and impact (heterophasic) copolymers.

In certain embodiments of the present invention, 50% to 20% by weight of the antioxidants of the present invention are added to the polyolefin. In certain other embodiments of the present invention, 10% to 5% by weight of the antioxidants of the present invention are added to the polyolefin. In certain other embodiments of the present invention, 0.1% to 2% by weight of the antioxidants of the present invention are added to the polyolefin. In certain other embodiments of the present invention, 0.001% to 0.5% by weight of the antioxidants of the present invention are added to the polyolefin. This percentage varies depending upon their end application and type of the polyolefin.

In certain embodiments of the present invention the antioxidants of the present invention are usually added to the polyolefin with stirring at between 0 and 100° C., between 10 and 80° C., between 20-30° C. or at room temperature.

In certain embodiments the antioxidants of the present invention can be mixed with other antioxidants or additives to produce formulations, such as those described in Provisional Patent Application No. 60/742,150, filed Dec. 2, 2005, Title: Lubricant Composition, by Kumar, Rajesh, et al., and Provisional Patent Application No. 60/731,325, filed Oct. 27, 2005, Title: Stabilized Polyolefin Composition, by Kumar, Rajesh, et al., the entire contents of each of which are incorporated herein by reference.

In certain embodiments the present invention relates to a method of preventing oxidation comprising combining an oxidizable material with a compound described herein.

In certain embodiments, the oxidizable material is an organic polymer or plastic. In certain embodiments, the oxidizable material is an elastomer. In certain embodiments, the oxidizable material is a lubricant. In certain embodiments, the oxidizable material is a petroleum based product. In certain embodiments, the oxidizable material is an edible oil or cooking oil. In certain embodiments, the oxidizable material is a cosmetic. In certain embodiments, the oxidizable material is a processed food product.

EXEMPLIFICATION

Example 1

Figure 2:
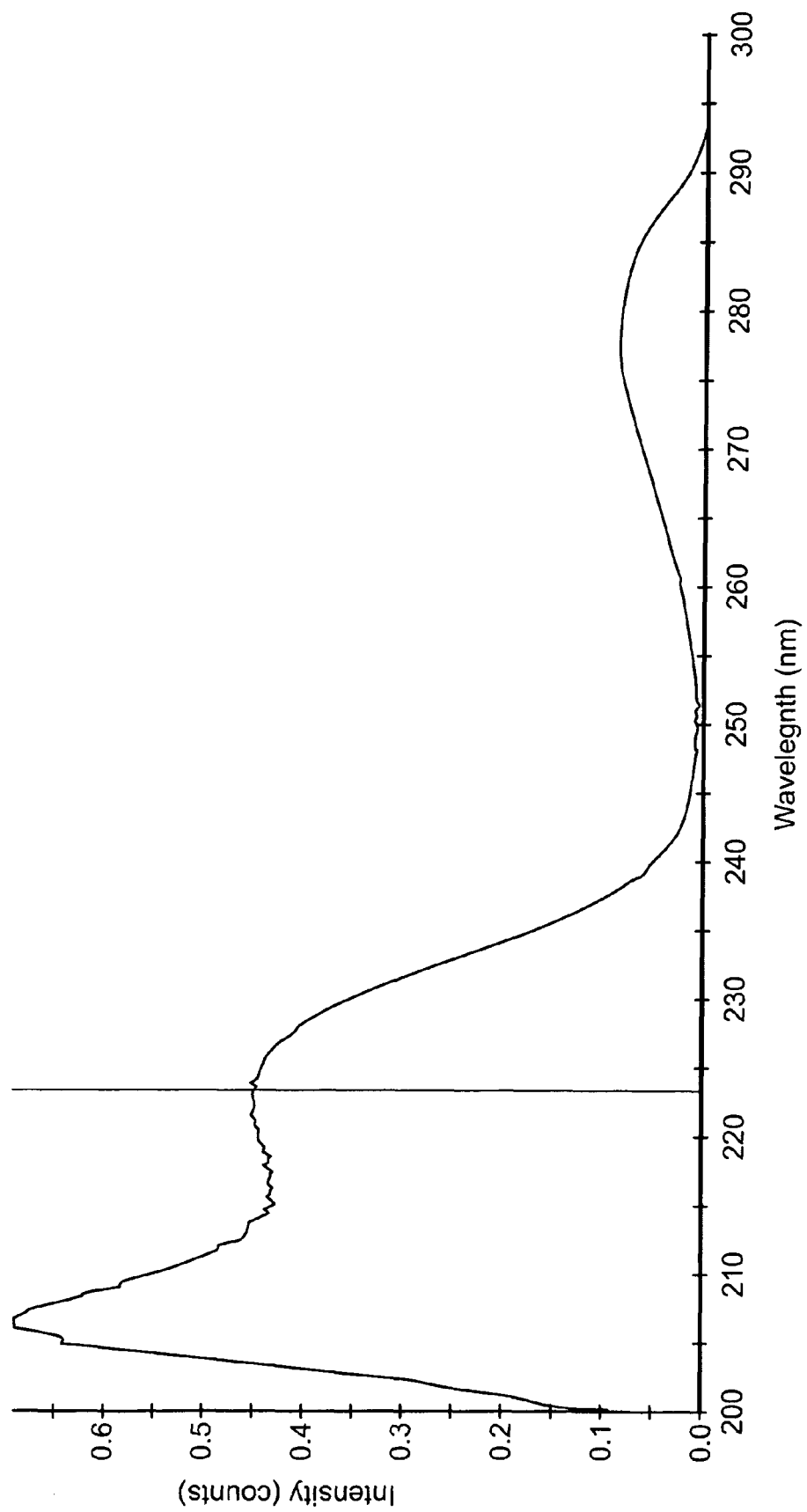
FIG. 2 is a UV spectrum of a tyramine based product of the present invention.
Figure 3:
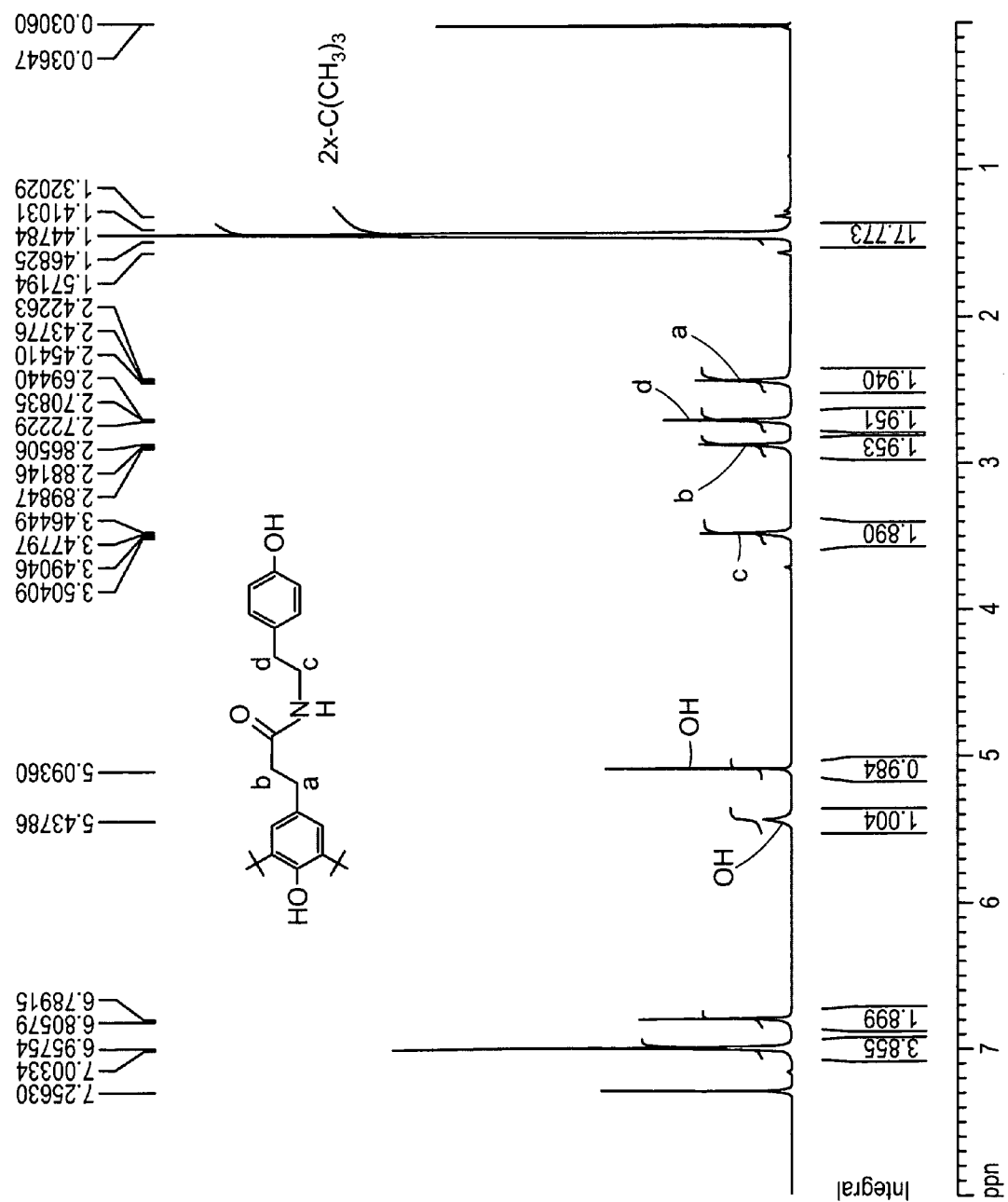
FIG. 3 is a $^1$H NMR spectrum of a tyramine based product of the present invention.

Synthesis of Tyramine Based AO 11.7 g of butylated hydroxytoluene (BHT) propanoic acid and 0.3 g of boric acid was dissolved in 50 ml of toluene and refluxed using a Dien Stark's apparatus for 30 minutes. To this solution was added 5.0 g of tyramine and the resulting solution was refluxed at 130° C. The water formed during the reaction was removed using Dien Stark's apparatus. The reaction was monitored by thin layer chromatography. After completion of the reaction, toluene was removed by distillation under reduced pressure and the solid obtained was re-dissolved in methanol. The solution in methanol was added drop wise to acidic water to remove any unreacted amine component. The precipitated solid was filtered and re-dissolved in methanol and added to basic water to remove any unreacted acidic component. The solid obtained was filtered, dried and analyzed by its spectral analysis, as shown in FIG. 1-3.

Example 2

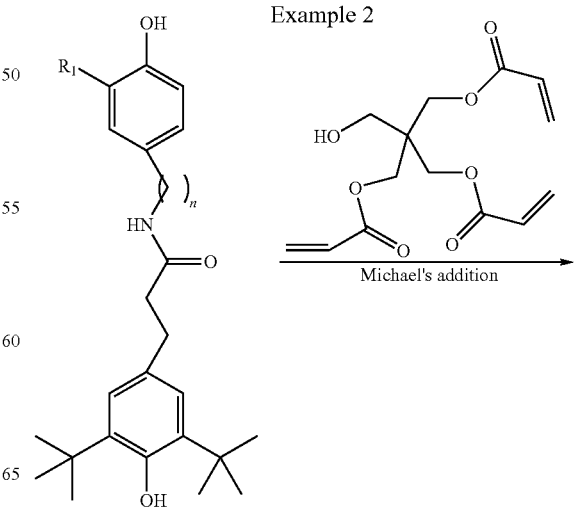

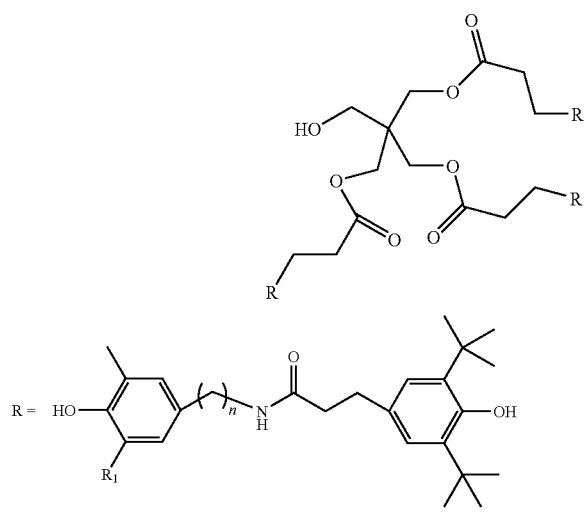

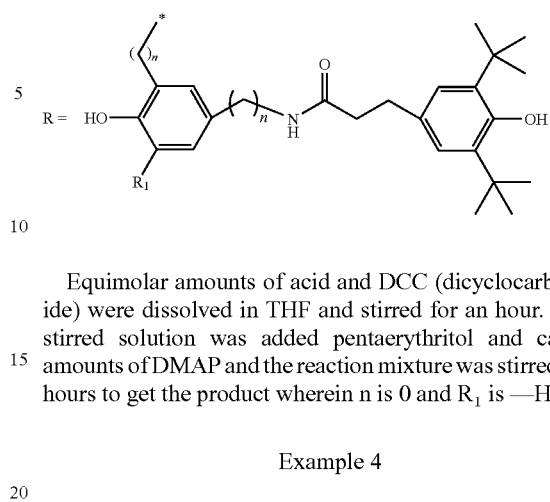

R₁ = H or alkyl group

The resultant compound wherein n is 0 and R₁ is Me was synthesized by dissolving the phenol in THF in the presence of potassium-t-butoxide and reacting the resultant carbanions with the acrylate under Michael's addition reaction conditions.

Equimolar amounts of acid and DCC (dicyclocarbodiimide) were dissolved in THF and stirred for an hour. To this stirred solution was added pentaerythritol and catalytic amounts of DMAP and the reaction mixture was stirred for 24 hours to get the product wherein n is 0 and R₁ is —H.

Example 3

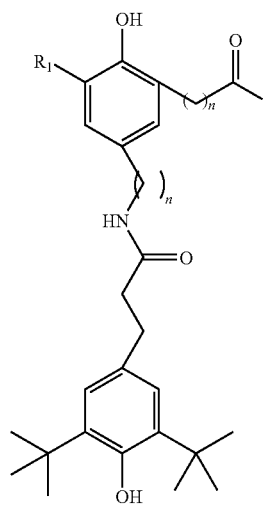

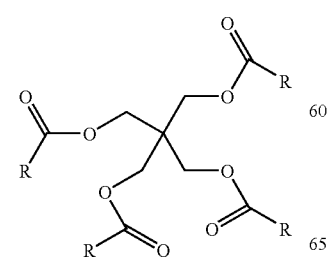

Example 4

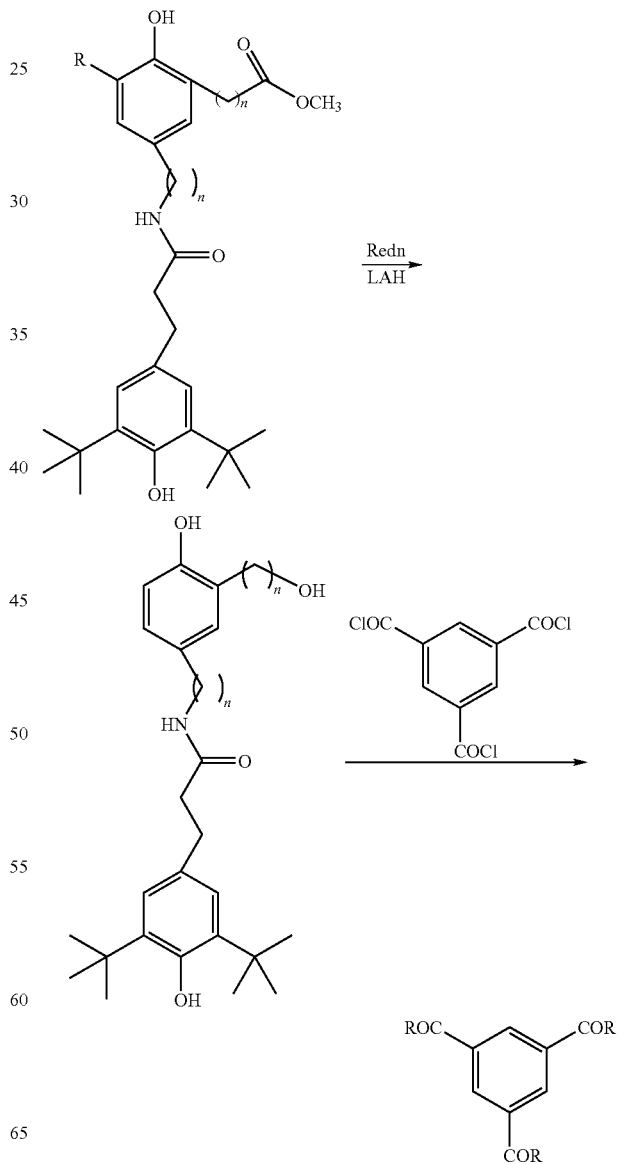

-continued

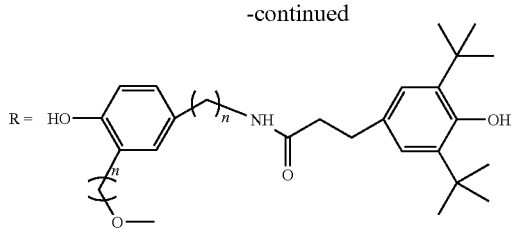

90 mg of lithium aluminium hydride was suspended in 5 ml of anhydrous THF under nitrogen atmosphere at 0° C. To this stirred suspension of LAH was added a solution of 700 mg of phenol methyl ester drop-wise while maintaining the temperature at 0° C. After complete addition, the reaction mixture was allowed to warm to room temperature and stirred for another 2 hours. After completion, the reaction was quenched by adding a mixture of methanol and water and the product alcohol was isolated by extraction with ethyl acetate. The alcohol wherein n is 0 was dried and characterized by its spectral analysis.

Example 5

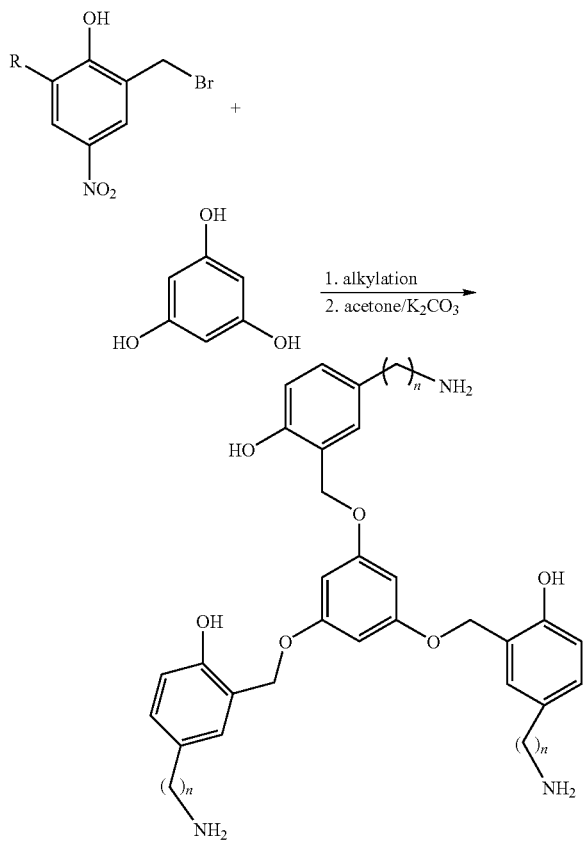

The compound shown above wherein n is 0 and R is H was prepared from trihydroxy benzene (phloroglucinol). Phloroglucinol was alkylated with, 5-nitro, 2-phenol benzyl bromide by dissolving in acetone in the presence of potassium carbonate.

The entire contents of each of the following are incorporated herein by reference.

Provisional Patent Application No. 60/632,893, filed Dec. 3, 2004, [now U.S. Pat. No. 7,678,877,] Title: Process For The Synthesis Of Polyalkylphenol Antioxidants, by Suizhou Yang, et al;

U.S. Publication No.: 2006/0128929 A1 published Jun. 15, 2006; patent application Ser. No. 11/292,813 filed Dec. 2, 2005, now published as U.S. Pat. No. 7,678,877, Title: Process For The Synthesis Of Polyalkylphenol Antioxidants, by Suizhou Yang, et al;

Provisional Patent Application No. 60/633,197, filed Dec. 3, 2004, Title: Synthesis Of Sterically Hindered Phenol Based Macromolecular Antioxidants, by Ashish Dhawan, et al.;

U.S. Publication No.: 2006/0128930 A1 published Jun. 15, 2006; patent application Ser. No. 11/293,050; filed Dec. 2, 2005, Title: Synthesis Of Sterically Hindered Phenol Based Macromolecular Antioxidants, by Ashish Dhawan, et al.;

Provisional Patent Application No. 60/633,252, filed Dec. 3, 2004, Title: One Pot Process For Making Polymeric Antioxidants, by Vijayendra Kumar, et al.;

U.S. Publication No.: 2006/0128939 A1 published Jun. 15, 2006; patent application Ser. No. 11/293,049; filed Dec. 2, 2005, Title: One Pot Process For Making Polymeric Antioxidants, by Vijayendra Kumar, et al.;

Provisional Patent Application No. 60/633,196, filed Dec. 3, 2004, Title: Synthesis Of Aniline And Phenol-Based Macromonomers And Corresponding Polymers, by Rajesh Kumar, et al.;

U.S. Publication No.: 2006/0128931 A1 published Jun. 15, 2006, now U.S. Pat. No. 7,902,317; patent application Ser. No. 11/293,844; filed Dec. 2, 2005, Title: Synthesis Of Aniline And Phenol-Based Macromonomers And Corresponding Polymers, by Rajesh Kumar, et al.;

U.S. Publication No.: 2006/0041094 A1 published Feb. 23, 2006; patent application Ser. No. 11/184,724, filed Jul. 19, 2005, Title: Anti-Oxidant Macromonomers And Polymers And Methods Of Making And Using The Same, by Ashok L. Cholli;

U.S. Publication No.: 2006/0041087 A1 published Feb. 23, 2006; patent application Ser. No. 11/184,716, filed Jul. 19, 2005, Title: Anti-Oxidant Macromonomers And Polymers And Methods Of Making And Using The Same, by Ashok L. Cholli;

U.S. Publication No.: 2006/0189824 A1 published Aug. 24, 2006, now U.S. Pat. No. 7,799,948; patent application Ser. No. 11/360,020, filed Feb. 22, 2006, Title: Nitrogen And Hindered Phenol Containing Dual Functional Macromolecules: Synthesis And Their Antioxidant Performances In Organic Materials, by Rajesh Kumar, et al.

U.S. Publication No.: 2006/0233741 A1 published Oct. 19, 2006, now U.S. Pat. No. 7,705,185; U.S. patent application Ser. No. 11/389,564, filed Mar. 24, 2006, Title: Alkylated Macromolecular Antioxidants And Methods Of Making, And Using The Same, by Rajesh Kumar, et al.

Provisional Patent Application No. 60/731,125, filed Oct. 27, 2005, Title: Macromolecular Antioxidants And Polymeric Macromolecular Antioxidants, by Ashok L. Cholli, et al.

Provisional Patent Application No. 60/731,021, filed Oct. 27, 2005, Title: Macromolecular Antioxidants Based On Sterically Hindered Phenols And Phosphites, by Ashok L. Cholli, et al.

Provisional Patent Application No. 60/742,150, filed Dec. 2, 2005, Title: Lubricant Composition, by Kumar, Rajesh, et al.

Provisional Patent Application No. 60/731,325, filed Oct. 27, 2005, Title: Stabilized Polyolefin Composition, by Kumar, Rajesh, et al.

U.S. Publication No.: 2005/0238789 A1 published Oct. 27, 2005, now U.S. Pat. No. 7,323,511; patent application Ser. No. 11/040,193, filed Jan. 21, 2005, Title: Post-Coupling Synthetic Approach For Polymeric Antioxidants, by Ashok L. Cholli, et al.;

WO Publication No.: WO/2005/070974 published Aug. 4, 2005; Patent Application No.: PCT/US2005/001948, filed Jan. 21, 2005, Title: Post-Coupling Synthetic Approach For Polymeric Antioxidants, by Ashok L. Cholli et al.;

WO Publication No.: WO/2005/071005 published Aug. 5, 2005; Patent Application No.: PCT/US2005/001946, filed Jan. 21, 2005, Title: Polymeric Antioxidants, by Ashok L. Cholli, et al.;

WO Publication No: WO/2003/087260 published Oct. 23, 20031 Patent Application No.: PCT/US03/10782, filed Apr. 4, 2003, Title: Polymeric Antioxidants, by Ashok L. Cholli, et al.;

U.S. Publication No.: 2004/0214935 A1 published Oct. 28, 2004, now U.S. Pat. No. 7,595,074; patent application Ser. No. 10/761,933, filed Jan. 21, 2004, Title: Polymeric Antioxidants, by Ashish Dhawan, et al.;

U.S. Publication No.: 2003/0230743 A1 published Dec. 18, 2003, now U.S. Pat. No. 7,233,432; patent application Ser. No. 10/408,679, filed Apr. 4, 2003, Title: Polymeric Antioxidants, by Ashok L. Cholli, et al.;

U.S. Pat. No. 6,770,785 B1

U.S. Pat. No. 5,834,544

Neftekhimiya (1981), 21 (2): 287-298.

While this invention has been particularly shown and described with references to preferred embodiments thereof, it will be understood by those skilled in the art that various changes in form and details may be made therein without departing from the scope of the invention.

EQUIVALENTS

Those skilled in the art will recognize, or be able to ascertain using no more than routine experimentation, many equivalents to specific embodiments of the invention described specifically herein. Such equivalents are intended to be encompassed in the scope of the following claims.

What is claimed is:

1. A compound represented by the following Structural Formula:

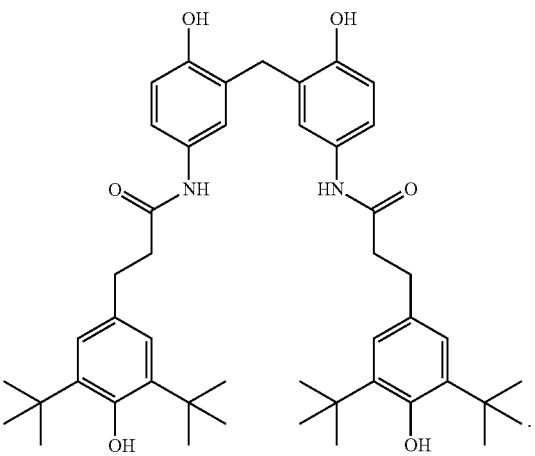

2. A compound represented by the following Structural Formula:

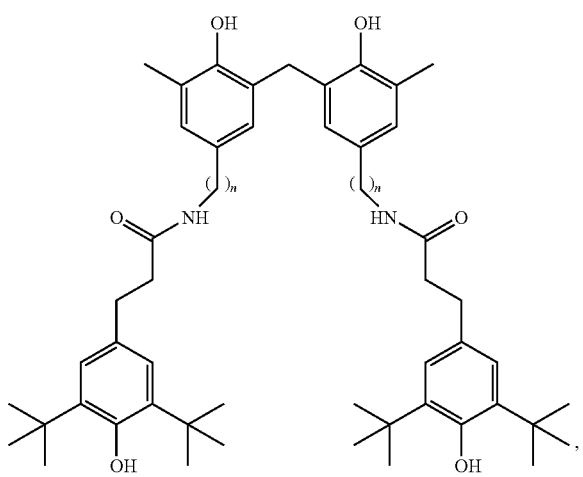

wherein n=1 to 4.

* * * * *